US00RE43472E

(19) United States
(12) Reissued Patent
Das et al.

(10) Patent Number: US RE43,472 E
(45) Date of Reissued Patent: Jun. 12, 2012

(54) TROPOMYOSIN ISOFORMS, AND DIAGNOSTIC AND THERAPEUTIC USES THEREFOR

(75) Inventors: Kiron M. Das, Basking Ridge, NJ (US); Jim Jung-Ching Lin, Iowa City, IA (US)

(73) Assignees: University of Medicine and Dentistry of New Jersey, Somerset, NJ (US); University of Iowa Research Foundation, Iowa City, IA (US)

(21) Appl. No.: 12/604,840

(22) Filed: Oct. 23, 2009

Related U.S. Patent Documents

Reissue of:
(64) Patent No.: 7,285,630
Issued: Oct. 23, 2007
Appl. No.: 10/201,501
Filed: Jul. 22, 2002

U.S. Applications:
(60) Provisional application No. 60/306,772, filed on Jul. 20, 2001.

(51) Int. Cl.
*C07K 14/00* (2006.01)

(52) U.S. Cl. ..... 530/350; 530/326; 530/387.1; 530/387.9; 530/806; 424/130.1; 424/139.1; 424/178.1; 424/185.1; 424/193.1; 435/7.1

(58) Field of Classification Search ..... None
See application file for complete search history.

(56) References Cited

FOREIGN PATENT DOCUMENTS

WO WO96/35449 A1 11/1996

OTHER PUBLICATIONS

Novy et al. "In vitro functional characterization of bacterially expressed human fibroblast tropomyosin isoforms and their chimeric mutants" Cell Motil Cytoskeleton (1993) 26:248-261.*

Das et al. "Expression of a novel human tropomyosin isoform, TC22, in dysplasia and carcinoma of the colon" Gastroenterology (Apr. 2001) vol. 120, No. 5, Supp.[1], pp. A161.*

Yokoyama, W. M. "Production of monoclonal antibodies" in Current Protocols in Immunology, John Wiley and Sons, Inc., (1995) 2.5.1-2.5.17.*

Dufour et al. "Splicing of two internal and four carboxyl-terminal alternative exons in nonmuscle tropomyosin 5 pre-mRNA is independently regulated during development" J. Biol. Chem. (1998) 273:18547-18555.*

Copper et al., "Production of antibodies" in Current Protocols in Immunology, John Wiley and Sons, Inc., (1995) 2.4.1-2.4.9.*

Zhang et all., "Purification of recombinant proteins and study of protein interaction by epitope tagging" in Current Protocols in Molecular Biology, John Wiley and Sons, Inc., (1998) 10.15.1-10.15.9.*

Perry S.V. "Vertebrate tropomyosin: distribution, propetries, and function" J. Muscle Res. Cell Motil. (2001) 22:5-49.*

Skolnick et al. "From genes to protein structure and function: novel applications of computational approaches in the genomic era" (2000) Trends in Biotechnology, 18:34-39.*

Bharadwaj et al., Cancer Letters, 2005, 229:253-260.*

Bharadwaj et al., J. Biol. Chem., 2004, 279:14039-14048.*

Brown et al., Proc. Acad. Natt. Sci. USA, 2005, 102:18878-18883.*

* cited by examiner

*Primary Examiner* — Michael Szperka
(74) *Attorney, Agent, or Firm* — Fox Rothshild LLP; Shahnam Sharareh

(57) ABSTRACT

A novel isoform of tropomyosin is disclosed. The isoform is closely related to epithelial human tropomyosin (hTM) and more particularly to hTM5 except the last coding exon. The novel isoform, is called TC22. Northern blot analysis with TC22-specific probe revealed that normal culture cell lines and normal epithelial tissues expressed very little, if at all, TC22 message, whereas their transformed counterparts and tumor tissues including dysfunction of the alimentary canal, significantly increased the expression of TC22. Assays directed at determining the level of TC22 are useful in diagnostics and therapeutics of dysfunction of the alimentary canal. Specific antibodies and mimics for TC22 are also disclosed for use in diagnostics and therapeutics of dysfunction of the alimentary canal.

17 Claims, 11 Drawing Sheets

FIG. 1

(A)

```
        aa#222                      aa#247
TC22    ERLYSQLERNRLLSNELKLTLHDLCD
hTM5    DK-KCTK-EHLCTQRM-DQ--L--NEM
hTM4    -K-AQAK-E-VG-HQT-DQ--NE-NCI
hTM5a   -KVAHAK-E-LSMHQM-DQ--LE-NNM
        aa#258                       aa#284
hTM1    -T-A-AK-E-VEIHQT-DQ--LE-NNL
```

(B)

```
        aa#222                      aa#247
TC22    ERLYSQLERNRLLSNELKLTLHDLCD
rNM4    ----------------------G---
rTMBr   DQ--H---Q--R-T-----A-NED
cTMBr   DQ--Q---Q-SR-T-----A-NED
        aa#38                       aa#63
LM      R--S----TQKT-V-D-FVV---V-R
```

(C)

```
TC22  TGGGCAGGGC TCAATGATGC"CCATTAAACT GAGCTTACTG CTCACACCAC 805
       GGGC GGGC TC  TGATGC CCA TAAAC               CACACCAC
rNM4  CGGGCCGGGC TCCCTGATGC CCAGTAAAC. .........., .CCACACCAC 800

TC22  TGACCTGGAC CCCAACAAAA AGCTGATTGT CTTTTTAAAA GTTATTATTT 855
      TGACCTGGAC CC A C AAA AGCTGA TG  CTTTT AAAA GT A T TT
rNM4  TGACCTGGAC CC.AGCCAAA AGCTGACTGC CTTTTAAAAA GTCACTGTTC 849

TC22  TAGCCCTGAG CAAATTGCAT TTTAATTGGG GCAGTTAGAA ...TGTTGAT 902
        GCCCT AG CAA TTGC T TTTAAT  GG GCAG TAGA     TGTTGAT
rNM4  ..GCCCTAAG CAAGTTGCTT TTTAATGAGG GCAGCTAGAC TACTGTTGAT 897

TC22  TTCCTAACAG CATTGTGAAG TTGACCATTG TGAAGTTTCT GTCCTTTAGA 952
      TTCCT  CAG C    T  A   T  C AT G   A    T T  T  T TAGA
rNM4  TTCCTGGCAG CCCCCTTCAA GTTGCAATGG CTA....TTT CTATTCTAGA 943

TC22  AGAGATTATG GGTGAAGAAG GGAGGGGCCT GAGAGATTAT AGTGAGAAAA 1002
      AGAGATT TG GGTGA GAAG AT GGGGCCT G GAG TT T AGTG  A AA
rNM4  AGAGATTGTG GGTGATGAAG AT.GGGGCCT GGGAGGTT.T AGTGC.AGAA 990

TC22  CTTGCGAGAA TTTTGTTTTC CACCCTTATT TGCTGCTCTT TCACTTGGGC 1052
      CTTG  A                ACC TTA   TGC GC CT  TCAC TG
rNM4  CTTGAAA... .......... .ACCGTTAGC TGCAGCCCTC TCACCTGTAT 1026

TC22  ACTGACTGTA GGATATGTTC CCTTGCATGG ATGTTTT.TA ACAATAAAAG 1101
      ACTGACTGTA GG T TG TC  C TGCATGG  T TTTT TA ACAATAAAA
rNM4  ACTGACTGTA GGGTTTGCTC ACCTGCATGG TTATTTTCTA ACAATAAAAA 1076

TC22  GACTGACTTG 1111
       A
rNM4  CA........ 1078
```

FIG. 8A

```
   1 gggtgggcac catggctggg atcaccacca tcgaggcggt gaagcgcaag atccaggttc
  61 tgcagcagca ggcagatgat gcagaggagc gagctgagcg cctccagcga gaagttgagg
 121 gagaaaggcg ggcccgggaa caggctgagg ctgaggtggc ctccttgaac cgtaggatcc
 181 agctggttga agaagagctg gaccgtgctc aggagcgcct ggccactgcc ctgcaaaagc
 241 tggaagaagc tgaaaaagct gctgatgaga gtgagagagg tatgaaggtt attgaaaacc
 301 gggccttaaa agatgaagaa aagatggaac tccaggaaat ccaactcaaa gaagctaagc
 361 acattgcaga agaggcagat aggaagtatg aagaggtggc tcgtaagttg gtgatcattg
 421 aaggagactt ggaacgcaca gaggaacgag ctgagctggc agagtcccgt tgccgagaga
 481 tggatgagca gattagactg atggaccaga acctgaagtg tctgagtgct gctgaagaaa
 541 agtactctca aaaagaagat aaatatgagg aagaaatcaa gattcttact gataaactca
 601 aggaggcaga gacccgtgct gagtttgctg agagatcggt agccaagctg gaaaagacaa
 661 ttgatgacct ggaagagcgt ctctacagcc aacttgagcg aaaccgcctg ctttctaatg
 721 agctgaagct aacgctgcat gatctgtgtg actgatgggc agggctcaat gatgcccatt
 781 aaactgagct tactgctcac accactgacc tggaccccaa caaaaagctg attgtctttt
 841 taaaagttat tattttagcc ctgagcaaat tgcattttaa ttggggcagt tagaatgttg
 901 atttcctaac agcattgtga agttgaccat tgtgaagttt ctgtccttta gaagagatta
 961 tgggtgaaga agggaggggc ctgagagatt atagtgagaa aacttgcgag aattttgttt
1021 tccaccctta tttgctgctc tttcacttgg gcactgactg taggatatgt tcccttgcat
1081 ggatgttttt aacaataaaa ggactgactt gaaaaaaaaa aaaaaaaaaa a
```

FIG. 8B

```
   1 magittieav krkiqvlqqq addaeeraer lqrevegerr areqaeaeva slnrriqlve
  61 eeldraqerl atalqkleea ekaadeserg mkvienralk deekmelqei qlkeakhiae
 121 eadrkyeeva rklviiegdl erteeraela esrcremdeq irlmdqnlkc lsaaeekysq
 181 kedkyeeeik iltdklkeae traefaersv aklektiddl eerlysgler nrllsnelkl
 241 tlhdlcd
```

Day 0 Ficoll whole blood → Isolate PBMCs Plate 1 x $10^5$ PBMCs / well; add Ag (hTM5 or CaD40) to 6 replicate wells

Day 5 Add 1 U of rIL-2 / well

Day 7 Add 1 x $10^5$ mitomycin treated PBMCs / well ± Ag

Day 9 Pool replicate → Re-aliquot PBMCs to anti-IFN-γ capture plate

Day 12 Add detecting → anti-IFN-γ Absubstrate Add BCIP / NBT

Day 14 Examine plate by dissecting microscope

FIGURE 9.
Steps of the ELISPOT assay hTM5 CaD40 Medium Control

TROPOMYOSIN ISOFORMS, AND DIAGNOSTIC AND THERAPEUTIC USES THEREFOR

Matter enclosed in heavy brackets [ ] appears in the original patent but forms no part of this reissue specification; matter printed in italics indicates the additions made by reissue.

PRIORITY

The present application claims priority to Provisional Application No. 60/306,772 filed on Jul. 20, 2001.

GOVERNMENTAL SUPPORT

This work was supported by grants (DK47673 and HD18577) from National Institutes of Health, Bethesda, Md. The government may have certain rights in this invention.

FIELD OF THE INVENTION

The present invention relates to the field of molecular biology.

BACKGROUND OF THE INVENTION

Numbers in parentheses represent references presented at the end of this specification. These references are incorporated as if fully set forth herein. The citation of any reference herein should not be construed as an admission that such reference is available as "Prior Art" to the instant application.

Tropomyosins are microfilament-associated proteins present in all eukaryotic cells with organ specific isoforms and distinct functions (1-3). A human fibroblast cell line expresses at least eight tropomyosin isoforms termed hTM1, hTM2, hTM3, hTM5a, hTM5a, hTM5b, hTM4, and hTM5, which are encoded by 4 different genes (3,4). The tropomyosin molecule is almost a fully α-helical protein with multiple heptad repeats and capable of forming a coiled coil dimer (5). These features appear to be associated with many known autoantibody epitopes and may contribute to autoantigenic potential (6). Indeed, several observations suggest that tropomyosin is an autoantigen for ulcerative colitis (7-10). Autoantibodies against tropomyosins are found in sera of individuals with ulcerative colitis (UC) and in IgG produced by the cultured lamina propria mononuclear cells that infiltrate the inflamed UC tissue. Furthermore, autoantibody to tropomyosin is also found in a mouse model for human UC, created by targeting deletion of the T-cell receptor α (TCRα) gene (11). Thus, the next questions are: which tropomyosin isoform or more specifically, which epitope can be recognized by these autoantibodies; and whether there is a specific tropomyosin isoform existing in UC tissue. Recently, using a limited number of tropomyosin isoform-specific monoclonal antibodies, it was demonstrated that colonic epithelial cells synthesize major tropomyosin isoforms of hTM4 and hTM5, whereas colonic smooth muscles contain at least hTM1, hTM2, and hTM3 isoforms (9). Using recombinant tropomyosin isoforms, it was further shown that UC patients produce significant autoantibodies preferentially against hTM5 (9,12).

Therefore, a need exists to identify sensitive and specific biomarkers for the diagnosis, to assess severity and predict the outcome of alimentary canal-related conditions in living subjects. Additionally, there is a clear need for new drug discovery assays, and for therapeutic agents for alimentary canal-related conditions that work quickly, potently, specifically, and with fewer side effects. Accordingly, it is toward the fulfillment of the foregoing and other objectives that the present invention is directed.

SUMMARY OF THE INVENTION

The present invention provides methods, materials and compositions for clinical screening, diagnosis, prognosis, therapy and prophylaxis of conditions involving the pathology of epithelial cells and particularly those of the alimentary canal, such as Barrett's esophagus, colon disease and dysfunction, and including ulcerative colitis and colon cancer, for monitoring the effectiveness of the treatment of such conditions, for selecting participants in clinical trials, for identifying patients most likely to respond to a particular therapeutic treatment and for screening and development of drugs for treatment of such alimentary canal-related conditions.

In accordance with a first aspect of the invention, a novel tropomyosin isoform (hereinafter "TI"), the isoforms identified as TC22, is disclosed. The full length of the TI of the invention is set forth in FIG. 8B and in Genbank at Accession No. AAF87083. Accordingly, the invention extends to the TI of the invention, and to analogs, mimics, variants and fragments thereof, including such materials as are immunogenic.

A particular fragment is defined by the C-terminal exon of the TI, identified as exon 9, including amino acids 222-247 set forth in FIGS. 1A, 1B and 8B, and that comprises the following sequence: ERLYSQLERNRLLSNELKLTLHDLCD (SEQ ID NO: 1). Suitable fragments further include and extend to the sequence just mentioned having a tag such as an N-terminal methionine or polyhistidine attached thereto.

In a second aspect of the invention, antibodies to the tropomyosin protein isoform are disclosed that are specific to the conditions of cancer of the alimentary canal and ulcerative colitis and are found in the epithelial cells. Representative antibodies include monoclonal and bispecific (chimeric) antibodies, and particular antibodies disclosed herein comprise mAbs TC22-2, TC22-4, TC22-6, and TC22-7, as non limiting examples. Of these TC22-4 is IgG while the other antibodies are IgM.

A further aspect of the invention provides methods of treating alimentary canal disease or dysfunction, including maladies of the stomach and rectum, comprising administering to a subject a therapeutically effective amount of an agent that modulates (e.g., upregulates or downregulates) the expression or activity (e.g. enzymatic or binding activity), or both, of a TI in subjects having such alimentary canal-related condition, in order to prevent or delay the onset or development of such condition, to prevent or delay the progression thereof, or to ameliorate the symptoms thereof.

A sixth aspect of the invention provides methods of screening for agents that modulate (e.g., upregulate or downregulate) a characteristic of, e.g., the expression or the enzymatic or binding activity, of a TI, a TI analog, a TI-related polypeptide, or an active fragment thereof. In particular, the invention contemplates the screening, such as by high-throughput techniques, for such agents that may affect the level of expression or activity of the TI of the present invention, and more specifically, a TI selected from the TI identified herein as TC22, having an amino acid sequence as set forth in FIG. 8B (SEQ ID NO: 2), and active fragments thereof, including the C-terminal domain and analogs thereof identified herein as exon 9, comprising amino acids 222-247, having an amino acid sequence as set forth in FIGS. 1A, 1B and 8B (SEQ ID NO: 2). Such agents could be used as part of a prognostic or diagnostic protocol or kit, to identify the likelihood or onset of a pathology associated with the alimentary canal and the epithelial tissue therein, such as for example, ulcerative colitis and cancer of the alimentary canal.

The antibodies described herein may be used to screen peptide libraries or haptens whereby the reactive peptides or haptens can then be isolated and tested for their ability to bind specifically to the TI's of the invention. Such peptides or haptens may be useful in therapies directed to the treatment of conditions such as ulcerative colitis and cancer of the alimentary canal. Once isolated and purified, such peptides can then be used to screen for other polyclonal or monoclonal antibodies or other molecules that may exhibit the same activities in relation to abnormal alimentary canal tissue, as described herein. The same materials would also function in prognostic and diagnostic tests and assays where the presence and level of expression of the TI's of the invention is being detected, measured or monitored as part of a surveillance of a particular alimentary canal condition.

Likewise, the invention includes haptens that may bind to the peptides, the antibodies and/or other relevant substrates and that may possess immunogenicity, so that they may also function as active components in diagnostic and therapeutic formulations.

In yet a further aspect of the invention the peptides can be formulated as pharmaceutical compositions with stabilizers to prevent proteolytic degradation, thus extending their half-life to be given orally, subcutaneously, intravenously, intranasally, intrathecally or as liposome preparations to mammals in need of such therapy.

The present invention also relates to methods of treating diseases or dysfunctions related to epithelial and alimentary canal tissue in mammals, such as ulcerative colitis and cancer of the alimentary canal, using the monoclonal antibodies, haptens, mimics, analogs, congeners, or active fragments thereof, of this invention.

The present invention also relates to a recombinant DNA molecule or cloned gene, or a degenerate variant thereof, which encodes a class of molecules that include the TI of the present invention and the fragment thereof defined by exon 9. More particularly, the DNA molecule may be selected from the sequence corresponding at least in part, to the sequence presented in FIG. 8A; DNA molecules or nucleic acids that code on expression for a protein having a sequence corresponding to at least a portion of the amino acid sequence of FIG. 8B, and DNA molecules or nucleic acids that code on expression for a protein having a sequence corresponding to at least a portion of the amino acid sequence of FIGS. 1A and 1B.

More particularly, the recombinant DNA molecule comprises a DNA sequence or degenerate variant thereof, which encodes a tropomyosin isoform, an analog thereof, a variant thereof, or an active fragment thereof, and which may be selected from the group consisting of:

(A) the DNA sequence encoding a protein having a sequence corresponding to at least a portion of the amino acid sequence of FIG. 8B (SEQ ID NO: 2);

(B) the DNA sequence encoding a protein having a sequence corresponding to at least a portion of the amino acid sequence of FIGS. 1A and 1B (SEQ ID NO: 1);

(C) the DNA sequence comprising the sequence of FIG. 8A (SEQ ID NO: 3);

(D) DNA sequences that hybridize to any of the foregoing DNA sequences under standard hybridization conditions; and (E) DNA sequences that code on expression for an amino acid sequence encoded by any of the foregoing DNA sequences.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present TI, which hosts could be used for diagnostic and drug discovery assays.

The invention includes an assay system for screening of potential drugs effective to modulate the level of expression or activity of the present TI by, for example, potentiating the activity of the present TI, the C-terminal domain and analogs thereof (exon 9), antibodies to the same, or active fragments thereof. In one instance, the test drug could be administered to a cellular sample with the ligand that suppresses or inhibits the expression or activity of the TI as defined herein, or an extract containing suppressed or bound TI, to determine its effect upon the binding activity of the TI or antagonists thereto, to any chemical sample (including DNA), or to the test drug, by comparison with a control.

The assay system could more importantly be adapted to identify drugs or other entities that are capable of binding to the TI, its mimics, analogs, or antagonists, and/or their targets, including peptides, haptens, other factors or proteins, whether found in the cytoplasm, the nucleus or elsewhere, thereby potentiating antibody activity, including e.g. the alimentary canal- associated therapeutic activities noted herein. Such assay would be useful in the identification of drug candidates from among peptide and other small molecule libraries, sera, and other relevant body fluids, and in the development of drugs that would be specific either in the promotion or the inhibition of particular cellular activity, or that would potentiate such activity, in time or in level of activity. For example, such drugs might be used to prevent or treat ulcerative colitis or cancer of the alimentary canal, or to treat other pathologies or injuries, associated with the alimentary canal and/or the related epithelium.

Thus, the present TI, the C-terminal domain and analogs thereof, and any antagonists or antibodies that may be raised thereto, are capable of use in connection with various diagnostic techniques, including immunoassays, such as a radioimmunoassay, ELISA, and ELISPOT, using for example, an antibody to the TI, the C-terminal domain and analogs thereof, or antagonists thereof, that has been labeled by either radioactive addition, or radioiodination, biotin biotinylation and other labeling techniques.

In an immunoassay, a control quantity of the TI, the C-terminal domain and analogs thereof, antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

In the instance where a radioactive label, such as the isotopes $^{3}H$, $^{14}C$ $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

The present invention includes an assay system which may be prepared in the form of a test kit for the quantitative analysis of the extent of the presence of the present TI, the C-terminal domain and analogs thereof, and/or antibodies thereto, or to identify drugs or other agents that may mimic or block their activity. The system or test kit may comprise a labeled component prepared by one of the radioactive and/or enzymatic techniques discussed herein, coupling a label to the TI, the C-terminal domain and analogs thereof, their agonists and/or antagonists, and one or more additional immunochemical reagents, at least one of which is a free or immobilized ligand, capable either of binding with the labeled component, its binding partner, one of the components to be determined or their binding partner(s).

In a further embodiment, the present invention relates to methods and associated kits for the detection of the presence or onset of maladies involving alimentary canal-associated disease and/or dysfunction in a subject, including humans, by gathering a biological sample from the subject and contacting the sample with a reagent comprising a preparation containing at least one antibody of the present invention, immunospecific derivatives, analogs, or fragments thereof. The biological samples tested in this manner may include biopsied tissue, body fluids such as serum or urine, or stool. The reagent may be labeled as described herein, or as well known in the art, or may reside in a kit with a suitable binding partner or substrate that is labeled. Such kits are described herein and are contemplated as part of the invention.

Accordingly, it is a principal object of the present invention to provide a tropomyosin isoform (TI) or active fragment thereof, that is associated with alimentary canal and epithelial tissue therein, and that is present and indicative of disease or dysfunction thereof.

It is a further object of the present invention to provide the C-terminal domain and analogs thereof of a TI, which is associated with alimentary canal and epithelial disease or dysfunction, and that can serve as a target for detection and diagnosis of said disease or dysfunction, or as the focal point of a drug discovery assay.

It is a further object of the present invention to provide antibodies to the tropomyosin isoforms (TI), active fragments thereof, and the C-terminal domain and analogs thereof of a TI of the invention, including human antibodies and corresponding antibody peptides, haptens, analogs and active fragments thereof in purified form that exhibits immunospecific binding thereto and that can serve as both diagnostic and therapeutic agents in relation to alimentary canal-related conditions such as ulcerative colitis and cancer of the alimentary canal.

It is a further object of the present invention to provide a method for detecting the presence, amount and activity of the TI, active fragment thereof, and/or the C-terminal domain and analogs thereof, of a TI in mammals in which invasive, spontaneous, or idiopathic pathological states are suspected to be present.

It is a further object of the present invention to provide a method and associated assay system for screening substances such as drugs, agents and the like, potentially effective in either mimicking the activity of the antibodies and/or their fragments, or the like, or for inhibiting the development and progression of disease or dysfunction of the alimentary canal, stomach or rectum, in mammals.

It is a still further object of the present invention to provide pharmaceutical compositions, based on the antibodies of the present invention and/or reactive with the TI or C-terminal domain and analogs thereof, of a TI comprising the same, for use in therapeutic methods which comprise or are based thereon, and including the antibodies, fragments, including peptide fragments, haptens, subunits, agonists, binding partner(s), or upon agents or drugs that control the production, or that mimic or antagonize the activities of the TI, active fragment, or the herein C-terminal domain and analogs thereof of a TI.

Other objects and advantages will become apparent to those skilled in the art from a review of the following description which proceeds with reference to the following illustrative drawings.

BRIEF DESCRIPTION OF THE FIGURES

FIG. 1 presents a comparison of amino acid sequences at the last coding exon and nucleotide sequence at the 3'-non-coding region of TC22 isoform with sequences found in other known nonmuscle tropomyosins. The last coding exon (amino acid residues from 222 to 247) of TC22 tropomyosin (SEQ ID NO:1) is compared with that of known human fibroblast tropomyosins (FIG. 1A) and that of rat and chick brain tropomyosin, as well as a sequence from gene 611.10 of Leishmania major (FIG. 1B). hTM5 (SEQ ID NO:4), hTM4 (SEQ ID NO:5), hTM5a (SEQ ID NO:6), and hTM1 (SEQ ID NO:7), human fibroblast tropomyosin isoform 5 (40), 4 (41), 5a (4) and 1 (42,43), respectively. In addition, human fibroblast tropomyosin isoform hTM5a, hTM5b, hTM2, hTM3, and hTMsmα have identical sequences in this region (4,44, 45). rNM4 (SEQ ID NO:8), rat cochlea non-muscle tropomyosin NM-4 (22); rTMBr (SEQ ID NO:9) and cTMBr (SEQ ID NO:10), rat (23) and chick (24), respectively, brain tropomyosin isoforms; LM (SEQ ID NO:11), amino acid residues from 38 to 63 of Leishmania major gene 611.10 (accession number AAF73087). Dashes indicate identities, and nonidentities are indicated by the single letter amino acid code relative to TC22. (FIG. 1C) Comparison of the 3'-non-coding sequence found in T22 (SEQ ID NO:12) and rat cochlea nonmuscle tropomyosin NM-4 (rNM4; SEQ ID NO:13)(22). The middle row designates identities between two sequences. Dots in the top and bottom rows indicate gaps.

FIG. 8A is the full length mRNA of the Tropomyosin TC22 as set forth in Genbank Accession No. AY004867 (SEQ ID NO:3), and FIG. 8B is the corresponding full length translated protein as set forth in Genbank at Accession No. AAF87082 (SEQ ID NO:2).

FIG. 9 is stepwise presentation of the ELISPON assay of Example II.

DETAILED DESCRIPTION OF THE PREFERRED EMBODIMENTS

Figure 2:
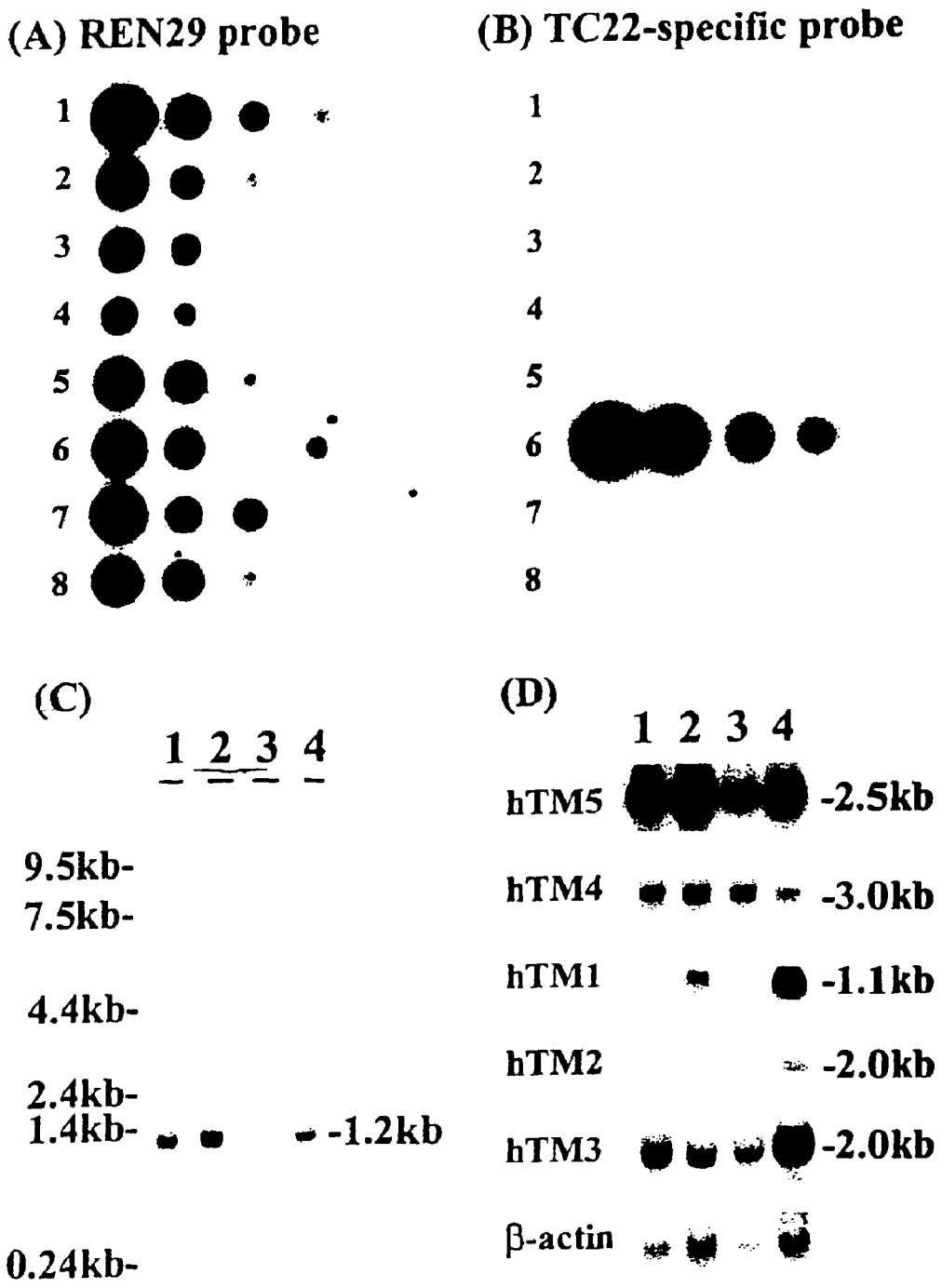
FIG. 2 presents Dot blot and Northern blot analyses. (A) and (B) show the dot blot results with labeled REN29 probe and TC22-specific probe, respectively, to demonstrate the TC22 probe specificity. Plasmid containing full-length cDNA insert of hTM1 (lane 1), hTM2 (lane 2), hTM3 (lane 3), hTM4 (lane 4), hTM5 (lane 5), TC22 (lane 6), hTMsmα (lane 7), or hTM5a (lane 8) was 5-fold serially diluted and spotted onto the nitrocellulose membrane at an amount from 20 ng to 0.16 ng. The hybridization with labeled REN29 probe (A), which recognized all known human tropomyosin isoforms (4), was used to demonstrate the cDNA loading of the blot. On the other hand, the hybridization with labeled TC22-specific probe showed that this probe recognized only TC22 but not hTM1, hTM2, hTM3, hTM5, hTMsmα, and hTM5a (B). (C) shows the Northern blot results when TC22-specific probe was used as probe on the blot membrane containing total RNAs isolated from LS180 (lane 1), T84 (lane 2), DLD-1 (lane 3), and EJ (lane 4) cells. The exposure time for this autoradiogram was 2.5 days. (D) o shows the Northern blot results when various tropomyosin isoform-specific probes and β-actin control probe were used as probes on the same or similar blot membrane as in (C). The description and specificity of these tropomyosin isoform-specific probes were reported previously (4). Only the portion of the blot containing the hybridized band of the corresponding RNA size was shown here. The exposure times for these autoradiograms were 16 hours for hTM5-, hTM4-, and hTM1-specific probe, 7 hours for hTM2-and hTM3-specific probe, and 45 minutes for β-actin control probe.

The present invention relates in one aspect to the discovery of a protein that has been observed in the alimentary canal, including humans, afflicted with disease and/or dysfunction of organs associated with the alimentary canal. Specifically, the present invention relates to the discovery of a tropomyosin isoform (TI) identified herein as TC22, its active fragment thereof, and to antibodies thereto, including immunospecific monoclonal antibodies, such as TC22-4 described herein.

TC22-was discovered from among colonic epithelial tropomyosins by extensively screening a cDNA library constructed from poly(A)+ RNAs of a human colon carcinoma cell line T-84. While the majority of clones isolated from this screening represented hTM4 and hTM5, there was a clone encoding a novel tropomyosin isoform which the applicants have named TC22, which is identical to hTM5 except as to the last C-terminal coding exon, exon 9. The identification of TC22 and the particular distinctive exon, afford the opportunity for the development of e.g. a drug discovery assay utilizing either or both material as the target. Likewise, either or both may be employed in either labeled or unlabeled form in diagnostic assays such as ELISA and sandwich assays, where competitive binding may be measured and would serve as an indication of the presence or progression of conditions where TI levels are measurable and/or elevated, such as the maladies discussed herein.

Accordingly, the isolation, sequencing and partial characterization of this novel tropomyosin isoform is presented herein, as well as the development of antibodies thereto, including monoclonal antibodies such as TC22-4, and the reactivity of this antibody in normal, inflammatory and cancerous alimentary canal tissues.

A further aspect of the invention provides methods for diagnosis of epithelial cell- and alimentary canal-related conditions as set forth herein that comprise detecting in a sample of tissue or body fluid the presence or level of at least one Tropomyosin Isoform (TI), an analog or variant thereof, or a fragment thereof, e.g., one or more of the TIs disclosed herein or any combination thereof, and more particularly, the TI identified herein, and/or the C-terminal fragment comprising exon 9, including amino acids 222-247, as set forth in FIGS. 1A, 1B and 8B (SEQ ID NO: 1). These methods are also suitable for clinical screening, prognosis, monitoring the results of therapy, identifying patients most likely to respond to a particular therapeutic treatment, drug screening and development, and identification of new targets for drug treatment.

A still further aspect of the invention provides antibodies, e.g., polyclonal, monoclonal, and chimeric (bispecific) antibodies capable of immunospecific binding to an antigen selected from a TI, e.g., the TI of the present invention, agonists thereof, mimics thereof, analogs thereof, immunogenic variants thereof, allelic variants thereof, or fragments of any of the foregoing, such as the fragment disclosed herein and comprising amino acids 222-247 of the TI of FIGS. 1A, 1B and 8B. Particular antibodies have been identified and tested herein, and the invention accordingly extends to antibodies, which antibodies are exemplified by monoclonal antibodies TC22-2, TC22-4, TC22-6 and TC22-7, of which TC22-4 is $IgG_1$ while the remainder are IgM. The invention also provides in another aspect, an assay for screening other antibodies and related binding partners, including haptens and peptide analogs, that may exhibit a like therapeutic activity. Such activities would include the treatment or prevention of alimentary canal-associated injuries or dysfunctions such as cancer of the alimentary canal and ulcerative colitis.

In accordance with the present invention there may be employed conventional molecular biology, microbiology, and recombinant DNA techniques within the skill of the art. Such techniques are explained fully in the literature. See, e.g., Sambrook et al., "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Cells, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Harnes & S. J. Higgins eds. (1985)]; "Transcription And Translation" [B. D. Haines & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The term "alimentary canal" as used herein refers to all anatomy and physiology associated with the digestive tract from the mouth to the anus.

The term "tTI analog" as used herein refers to a polypeptide that possesses similar or identical function(s) as a TI but need not necessarily comprise an amino acid sequence that is similar or identical to the amino acid sequence of the TI, or possess a structure that is similar or identical to that of the TI. As used herein, an amino acid sequence of a polypeptide is "similar" to that of a TI if it satisfies at least one of the following criteria: (a) the polypeptide has an amino acid sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the amino acid sequence of the TI; (b) the polypeptide is encoded by a nucleotide sequence that hybridizes under stringent conditions to a nucleotide sequence encoding at least 5 amino acid residues (more preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues) of the TI; or (c) the polypeptide is encoded by a nucleotide sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleotide sequence encoding the TI. As used herein, a polypeptide with "similar structure" to that of a TI refers to a polypeptide that has a similar secondary, tertiary or quartemary structure as that of the TI. The structure of a polypeptide can determined by methods known to those skilled in the art, including but not limited to, X-ray crystallography, nuclear magnetic resonance, and crystallographic electron microscopy.

The term "derivative" as used herein refers to a polypeptide that comprises an amino acid sequence of a second polypeptide which has been altered by the introduction of amino acid residue substitutions, deletions or additions. The derivative polypeptide possesses a similar or identical function as the second polypeptide.

The term "fragment" as used herein refers to a peptide or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a second polypeptide. The fragment of a TI may or may not possess a functional activity of the a second polypeptide.

The term "isoform" as used herein refers to variants of a polypeptide that are encoded by the same gene, but that differ in their pI or MW, or both. Such isoforms can differ in their amino acid composition (e.g. as a result of alternative mRNA or pre-mRNA processing, e.g. alternative splicing or limited proteolysis) and in addition, or in the alternative, may arise from differential post-translational modification (e.g., glycosylation, acylation, phosphorylation). As *used herein, the term "isoform" also refers to a protein that exists in only a single form, i.e., it is not expressed as several variants. The term "modulate" when used herein in reference to expression or activity of a TI or a TI-related polypeptide refers to any change, e.g., upregulation or downregulation, of the expression or activity of the TI or a TI-related polypeptide. Based on the present disclosure, such modulation can be determined by assays known to those of skill in the art or described herein.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=# of identical positions/total # of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Aca. Sci. USA 90:5873-5877. The NBLAST and XBLAST programs of Altschul, et al. (1990), J. Mol. Biol. 215:403-410 have incorporated such an algorithm. BLAST nucleotide searches can be performed with the NBLAST program, score=100, wordlength=12 to obtain nucleotide sequences homologous to a nucleic acid molecule of the invention. BLAST protein searches can be performed with the XBLAST program, score=50, wordlength=3 to obtain amino acid sequences homologous to a protein molecule of the invention. To obtain gapped alignments for comparison purposes, Gapped BLAST can be utilized as described in Altschul et al. (1997) Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See ncbi.nlm.nih.gov of the world-wide web.

Another example of a mathematical algorithm utilized for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

Also, the terms "tropomyosin isoform," "TI", "antibody," "antibody peptide,""peptide," "hapten" are intended where appropriate, to include within their scope proteins specifically recited herein as well as all substantially homologous analogs and allelic variations.

The term "dysfunction," when used alone, includes any pathology, including disease and injury, of the organ or system to which the dysfunction relates.

Also within the scope of the present invention are DNA sequences encoding a TI of the invention, the C-terminal domain and analogs thereof of a TI, or a peptide analog, hapten, or active fragment thereof, which code for a peptide that defines in at least a portion thereof, or has the same amino acid sequence as set forth in FIGS. 1A, 1B and 8B, but which are degenerate to the same sequence(s). By "degenerate to" is meant that a different three-letter codon is used to specify a particular amino acid.

Amino acid substitutions may also be introduced to substitute an amino acid with a particularly preferable property. For example, a Cys may be introduced as a potential site for disulfide bridges with another Cys. A H is may be introduced as a particularly "catalytic" site (i.e., H is can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

As used herein, the term "antibody" is any immunoglobulin, including antibodies and fragments thereof, that binds a specific epitope. The term is intended to encompass polyclonal, monoclonal, and chimeric antibodies, the last mentioned described in further detail in U.S. Pat. Nos. 4,816,397 and 4,816,567. Such antibodies include both polyclonal and monoclonal antibodies prepared by known generic techniques, as well as bi-specific (chimeric) antibodies, and antibodies including other functionalities suiting them for additional diagnostic use conjunctive with their capability of modulating activity, e.g. that upregulates or downregulates TI activity or expression, or that modulates the presence or progression of disease or dysfunction associated with such TI activity or expression. An "antibody combining site" is that structural portion of an antibody molecule comprised of heavy and light chain variable and hypervariable regions that specifically binds antigen. The phrase "antibody molecule" in its various grammatical forms as used herein contemplates both an intact immunoglobulin molecule and an immunologically active portion of an immunoglobulin molecule. Exemplary antibody molecules are intact immunoglobulin molecules, substantially intact immunoglobulin molecules and those portions of an immunoglobulin molecule that contains the paratope, including those portions known in the art as Fab, Fab', $F(ab')_2$ and F(v).

Fab and $F(ab')_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from $F(ab')_2$ portions followed by reduction of the disulfide bonds linking the two heavy chains portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bi-specific (chimeric) monoclonal antibody.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against the TI of the invention or an active fragment of a TI such as exon 9, can be screened for various properties; i.e., isotype, epitope, affinity, etc. Of particular interest are monoclonal antibodies that exhibit the same activity as the monoclonal antibodies of the present invention, and particularly monoclonal antibody TC22-4.

An anti-TI antibody that may be used in the diagnostic methods of this invention may be an affinity purified polyclonal antibody. More preferably, the antibody is a monoclonal antibody (mAb). In addition, it is preferable for the anti-peptide antibody molecules used herein be in the form of Fab, Fab', $F(ab')_2$ or F(v) portions of whole antibody molecules.

As suggested earlier, the diagnostic method of the present invention comprises examining a cellular sample, medium or body fluid or material by means of an assay including an effective amount of an antibody to a TI, the C-terminal domain and analogs thereof of a TI as set forth herein, or a suitable analog such antibody or antagonist, such as an affinity-purified polyclonal antibody, and more preferably a mAb. In addition, it is preferable for the antibody molecules used herein be in the form of Fab, Fab', $F(ab')_2$ or F(v) portions or whole antibody molecules. As previously discussed, patients capable of benefiting from this method include those suffering from conditions such as ulcerative colitis and cancer of the alimentary canal. Methods for isolating the peptides and inducing anti-peptide antibodies and for determining and optimizing the ability of antipeptide antibodies to assist in the examination of the target cells are all well-known in the art.

Methods for producing polyclonal antibodies are well-known in the art. See U.S. Pat. No. 4,493,795 to Nestor et al. A monoclonal antibody, typically containing Fab and/or $F(ab')_2$ portions of useful antibody molecules, can be prepared using the hybridoma technology described in Antibodies—A Laboratory Manual, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with an antibody peptide-binding portion thereof, or the antibody peptide or fragment, or an origin-specific DNA-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact in the same fashion as the present antibodies and their ability to inhibit or promote specified activity in target cells and tissues.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. In the present instance and as set forth in the examples herein, the antibodies may be raised by priming with both the full length TI and a quantity of the C-terminal domain isolate and analogs thereof. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., Virol. 8:396 (1959)) supplemented with 4.5 gm/l glucose, 20 mm glutamine, and 20% fetal calf serum. An exemplary inbred mouse strain is the Balb/c.

Methods for producing monoclonal anti-peptide antibodies are also well-known in the art. See Niman et al., Proc. Natl. Acad. Sci. USA, 80:4949-4953 (1983). Typically, the present peptide, or a peptide analog or fragment, is used either alone or conjugated to an immunogenic carrier, as the immunogen in the before described procedure for producing anti-peptide monoclonal antibodies. The hybridomas are screened for the ability to produce an antibody that immunoreacts with the peptide and thereby reacts similarly to the antibodies of the present invention.

A variety of assays may be used that are well known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination). In the production of antibodies, screening for the desired antibody can be accomplished by techniques utination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Antibodies can be labeled for detection in vitro, e.g., with labels such as enzymes, fluorophores, chromophores, radioisotopes, dyes, colloidal gold, latex particles, and chemiluminescent agents. Alternatively, the antibodies can be labeled for detection in vivo, e.g., with radioisotopes (preferably technetium or iodine); magnetic resonance shift reagents (such as gadolinium and manganese); or radioopaque reagents.

The labels most commonly employed for these studies are radioactive elements, enzymes, chemicals which fluoresce when exposed to ultraviolet light including protein materials such as green fluorescent protein (GFP), and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The polypeptide can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

Accordingly, in a first aspect of the diagnostic application of the present invention, a method is disclosed for detecting the presence or activity of a TI, active fragment thereof, or a C-terminal domain and analogs thereof of a TI; wherein said TI, fragment or C-terminal domain and analogs thereof is measured by:

A) contacting a biological sample from a mammal in which the presence or activity of said TI is suspected with a binding partner of said TI under conditions that allow binding of said TI to said binding partner to occur; and B) detecting whether binding has occurred between said TI from said sample and the binding partner;

wherein the detection of binding indicates that presence or activity of the TI in the sample.

In a variant aspect, the invention extends to a method for detecting the presence and activity of a polypeptide ligand associated with a given invasive stimulus in mammals in which the TI of the invention is believed to be implicated, comprising detecting the presence or activity of the TI as set forth above, where detection of the presence or activity of the TI indicates the presence and activity of a polypeptide ligand associated with a given invasive stimulus in mammals. In a particular aspect, the invasive stimulus is an infection, and may be selected from viral infection, protozoan infection, bacterial infection, tumorous mammalian cells, and toxins.

Correspondingly, the invention covers an assay method for screening drugs and other agents for ability to modulate the production or mimic the activities of a TI or active fragment thereof, and to thereby identify new agents for the treatment of disease or dysfunction associated with TI/TI fragment presence or activity, said method comprising:

A. culturing an observable cellular test colony inoculated with a drug or agent;

B. harvesting a supernatant from said cellular test colony; and

C. examining said supernatant for the presence of said TI wherein an increase or a decrease in a level of said TI indicates the ability of a drug to modulate the activity of said TI.

Lastly, a test kit is contemplated for the demonstration of a TI in a cellular sample, which kit comprises:

A. a predetermined amount of a detectably labelled specific binding partner of such TI;

B. other reagents; and

C. directions for use of said kit.

A variant test kit is disclosed for demonstrating the presence of a TI in a patient sample and thereby diagnosing the likelihood or onset of a disease or dysfunction associated with said TI. The kit comprises:

A. a predetermined amount of a TI or fragment thereof;

B. a predetermined amount of a specific binding partner of said TI, such as an antibody thereto;

C. other reagents; and

D. directions for use of said kit;

wherein either said TI or said specific binding partner are detestably labelled. Both of the above kits may utilize a labeled immunochemically reactive component selected from the group consisting of polyclonal antibodies to the TI, monoclonal antibodies to the TI, fragments thereof, and mixtures thereof.

The following examples are presented to describe the development and practice of the present invention, and are to be considered for purposes of illustration and not limitation.

EXAMPLE I

Isolation and Characterization of cDNA Clones

A λZAPII phage library prepared from T84 human colon cancer cell poly(A)$^+$ RNAs was purchased from STRATAGENE® (La Jolla, Calif). A 29-mer oligonucleotide probe common to all of known human tropomyosin mRNAs was used to screen this library. After plaque purification, 28 positive clones were obtained. Plasmids from positive plaques were isolated from their UNI-ZAP® XR vector by in vivo excision with helper phage as described by the manufacturer. The cDNA inserts were PCR amplified by using T3 and T7 primers. The PCR products were subjected to restriction enzyme (RE) analyses for classification of tropomyosin isoforms. Some of the classifications were also confirmed by PCR amplification with isoform-specific primers as listed in Table 1. DNA sequencing was performed using SEQUENASE® Kit version 2.0 (United States Biochemical, Cleveland, Ohio) and sequencing results were used as a final verification of tropomyosin isoforms. While the majority of clones represented hTM4, hTM5 and hTM1, a plasmid clone called pTC22 contained a full-length cDNA capable of encoding a novel tropomyosin isoform.

Construction of Expression Plasmids

To investigate the properties of the TC22 isoform, the TC22 insert released by NcoI/KpnI double digestion was further subcloned into bacterial expression vector pET8 c/s as described previously (14) to yield pETTC22. Both pETTC22 and previously constructed pEThTM5 (14) were transformed individually into the E. coli host BL21(DE3) LysS for the production of recombinant full-length TC22and hTM5, respectively. Bacterial cultures were grown and induced for respective protein production. The recombinant tropomyosins were purified by using a PHARMACIA® FPLC system with a MONO Q™ column and a hydroxylapatite column.

For the construction of eukaryotic expression plasmids that code green fluorescent protein (GFP)-tropomyosin fusion protein, PCR amplifications of the coding region of TC22 and hTM5 cDNA were performed with specific primer pairs flanking the translation start and stop sites. Since both TC22 and hTM5 cDNA are identical in the region from residues 1 to 222, the upstream primer containing an adapter EcoRI site (5'GTCGAATTCATGGCTGGGATCACCAC3'; SEQ ID NO:14) was used for both amplifications. The sequences for the downstream primers containing an adapter BamHI site include 5'GGTGGATCCTCAGTCACACAGATCATGC3'; SEQ ID NO:15 for TC22 and 5'GGTGGATCCTACATCTCATTCCAGGTCAAG3'; SEQ ID NO:16 for hTM5. The PCR products after digestion with EcoRI and BamHI were subcloned into the corresponding sites of pEGFPC2 vector (Clontech) to yield pGFPTC22 and pGFPhTM5. All of the subclones were verified by restriction enzyme site analysis, insert size and nucleotide sequencing.

Production of Monoclonal Antibodies Specific to the TC22 isoform

For monoclonal antibody production, a female Balb/C mouse was immunized intraperitoneally with 50 μg of purified TC22 emulsified in an equal volume of TITER-MAX® (CytRx Corp. Norcross, Ga.). At 21 days, the mouse was intraperitoneally boosted with a mixture of 15 μg of TC22 and 30 μg of TC22-specific peptide. The TC22-specific peptide from residue #223 to 247 of TC22 was synthesized at the Robert Wood Johnson Medical School peptide synthesis facility. The mouse was boosted 2 more times with TC22-specific peptide alone at the fifth and seventh week after immunization. At the eighth week, the mouse was bled from the tail, and the serum obtained was tested for antibody titers to TC22 and hTM5 by enzyme-linked immunosorbant assay (ELISA). The mouse with a differential serum titer to TC22 and hTM5 was sacrificed at 3 days after the last intravenous injection with TC22-specific peptide. Cell fusion, and hybridoma cloning were carried out. Four monoclonal antibodies (TC22-2, TC22-4, TC22-6, and TC22-7) preferentially recognizing TC22 over hTM5 were obtained. The TC22-4 is $IgG_1$ whereas the others are IgM class.

Cell Culture and DNA Transfection

Cell lines used in this example included: KD, a human lip fibroblast cell line; HuT-11, a chemically transformed derivative of KD; WI-38, a human fetal lung diploid cell line (ATCC CCL75); WI-38 VA13, a SV40 transformed derivative of WI-38 (ATCC CCL75.1); EJ, a human bladder carcinoma cell line; CHO, a Chinese hamster ovarian cell line; and human colon carcinoma cell lines, LS 180, T84, and DLD-1. All cells were grown in Dulbecco's modified Eagle's medium containing 10% fetal calf serum and maintained in a 37° C. humidified incubator with 95% air and 5% $CO_2$.

Plasmid DNAs (pGFPTC22 and pGFPhTM5) were transiently transfected into CHO cells grown on coverslips by using DOTAP transfection reagents (Boehringer-Mannheim Biochemicals, Indianapolis, Ind.). The coverslips containing the transfected cells were either directly mounted or fixed and mounted on glass slides for the observation under a fluorescence photomicroscope III. FITC-filters were used to visualize GFP fluorescence.

Dot Blot and Northern Blot Analyses

Dot blot analysis was performed. Briefly, plasmid DNA containing full-length cDNA insert for each tropomyosin isoform was 5-fold serially diluted and dotted on a nitrocellulose membrane at the amount from 20 ng to 0.16 ng. The probes used included REN29, which recognized all known human tropomyosin isoforms, and a TC22-specific probe, which contained 54 bp of coding region and 284 bp of 3'-noncoding region of TC22 cDNA. The plasmids used included pGEM-hTMI, pGEMhTM2, pGEMhTM3, pEThTM4, pEThTM5, pTC22, pSN42-3 and pSNL30-5. For Northern blot analysis, total RNAs were isolated from various human cell lines using the guanidine isothiocyanate procedure. A human tumor panel blot purchased from Invitrogen (Carlsbad, Calif.) containing 20 μg each of total RNAs from stomach, colon and rectal tumor tissues and their respective normal counterparts was also used to examine the expression of TC22 by Northern blot analysis. Northern blot was performed with various tropomyosin isoform-specific probes.

Tropomyosin-Enriched Protein Extracts of Colonic Mucosa from Patients

Tropomyosin-enriched fractions were prepared from the biopsy specimens of colonic mucosa obtained during colonoscopy from 5 normal (spastic colon), 9 patients with ulcerative colitis (UC), and 2 with Crohn's disease (CD). In addition, surgical specimens of 6 colon cancers were also used. In five of these patients, both tumor area and adjacent normal tissue were separately processed. In one, adjacent normal tissue was not available. Five μg of tropomyosin-enriched fractions was separated by 12% SDS-PAGE and used in Western blot analysis with monoclonal antibodies LC1 (anti-hTM5) and TC22-4 (anti-TC22). The epitope of LC1 was mapped to residues 4-10 of hTM5. Thus, the LC1 antibody should also recognize TC22 Immunocytochemical localization of TC22 was performed using a sensitive immunoperoxidase assay.

Identification of cDNA Clones Encoding Tropomyosin Isoforms from T84 Colon Cancer Cells Previously, a common oligonucleonde probe (REN29) was designed and it was demonstrated that this REN29 probe was capable of recognizing mRNAs derived from all 4 human tropomyosin genes. Novy R E, Lin J L-C, Lin C-S, Lin J J-L. Human fibroblast tropomyosin isoforms: characterization of cDNA clones and analysis of tropomyosin isoform expression in human tissues and in normal and transformed cells. CELL MOTIL. CYTOSKEL. 1993; 25:267-281. This probe was used to extensively screen a cDNA library prepared from T84 cancer cells, and 28 positive clones were obtained. After restriction enzyme analysis, PCR amplification with isoform-specific primers, and nucleotide sequencing of the inserts, 15, 11, and 1 clones were classified into hTM5, hTM4, and hTM1, respectively. Surprisingly, a clone, called TC22, had a cDNA insert of 1,131 bp (GenBank accession number AY004867), which contained most of sequences from nt #1 to nt #676 identical to hTM5. These included 11 bp of 5'-untranslated region, and 665 bp of coding region for amino acid residue 1 to residue 221. The divergent sequence contained 79 bp coding for the last alternatively spliced exon and 376 bp of 3'-untranslated region. This result suggests that both TC22 and hTM5 are derived from the same gene and use different C-terminal exons and 3'-untranslated regions.

TC22 Tropomyosin is a Novel Spliced Variant from the Human γ-TM Gene

TC22 message deduced from cDNA sequence was capable of coding a protein with 247 amino acid residues, which is one amino acid shorter than that predicted from hTM5 cDNA. FIG. 1A shows the amino acid sequence comparisons of the last coding exon in TC22 to that in all known human fibroblast tropomyosin isoforms including hTM1, hTM4, hTM5 and hTM5a. The sequence homology of this last coding exon was not particularly impressive, ranging from 26.9% to 34.6%. The other known human tropomyosin isoforms that are expressed in fibroblasts cells, such as hTM2, hTM3, hTMsmα and hTM5b have an identical sequence in this exon as that of hTM5a. Therefore, these results suggest that the TC22 isoform has a unique exon. When the GenBank database was searched against this exon, 4 different gene sequences were detected (FIG. 1B). There is a very high homology (96.1%) between the C-terminal exons of human TC22 and rat NM-4 (rNM4). Since the rNM4 isoform is an alternatively spliced tropomyosin isoform from the rat homologue of human hTM5 (or γ-TM) gene, this high homology supports the idea that both hTM5 and TC22 are encoded by the same γ-TM gene. However, further sequence comparison between TC22 and rNM4 isoforms suggests that the TC22 protein is not the equivalent form of rNM4 in the rat, because different internal, alternatively spliced exons are found in these isoforms. Moreover, as shown in FIG. 1C, the 3'-untranslated sequence contains extensive homologous regions between TC22 and rNM4, further confirming that TC22 is an alternatively spliced isoform of human γ-TM gene.

TC22 is Preferentially Expressed in Transformed Cell Lines and Tumor Tissues

In order to examine the expression of TC22 isoform in various cell lines and tissues, a TC22-specific probe containing the last coding exon and most of the 3'-noncoding sequence was used in dot blot and Northern blot analyses. In contrast to the REN29 probe, which recognized cDNAs from all known human fibroblast tropomyosins (FIG. 2A), this probe hybridized only to TC22 cDNA (FIG. 2B), as demonstrated by dot blot analysis. Furthermore, the TC22 probe hybridized to a 1.2 kb mRNA from three human colon cancer cell lines (LS 180, T84 and DLD-1) and one bladder cancer cell line (EJ) (FIG. 2C). These cell lines do express various tropomyosin isoforms with different message sizes (FIG. 2D), as detected in the Northern blot analysis with respective isoform-specific probes.

Northern blot analysis was performed on total RNA isolated from two pairs of normal and transformed cell lines with the TC22-specific probe. The results are presented in FIG. 3A. A single 1.2 kb mRNA was detected. The amounts of TC22 messages are clear in transformed cell lines, HuT-11 and WI-38 VA 13, as compared to their normal counterparts, KD and WI-38, respectively, where there is hardly any signal (compared lanes 1 and 3 to lanes 2 and 4, respectively, of FIG. 3A). The control for hybridization and RNA gel loading was performed with γ-actin as a probe (bottom panel of FIG. 3A). To further determine the expression of TC22 in normal and tumor tissues, a human tumor panel blot containing total RNAs isolated from three different human normal and tumor tissues was hybridized with the TC22-specific probe. The Northern blot results are shown in the top panel of FIG. 3B. Again, TC22 messages are significantly enhanced in stomach tumor (lane 1), colon tumor (lane 3), and rectal tumor (lane 5), as compared to their respective normal counterparts (lanes 2, 4, and 6 of FIG. 3B). The total RNA loading in each lane was visualized by ethidium bromide staining of the gel, which showed comparable amounts of 28S or 18S rRNAs in each lane (bottom panel of FIG. 3B). The preferential expression of TC22 in transformed cells and tumor tissues may provide a useful biomarker for cancer surveillance.

TC22 Isoform has a Weaker Affinity to Microfilament Bundles than hTM5 Isoform

To demonstrate the actin-binding property of TC22 tropomyosin, full-length TC22 cDNA was constructed into an eukaryotic expression vector, pEGFP C2. The resulting plasmid when transfected into CHO cells would express as a GFP-TC22 fusion protein. Using fluorescence microscopy, the association of fusion protein to microfilament bundles (stress fibers) can then be assessed. As a parallel control, full-length hTM5 cDNA was also constructed into pEGFP C2 vector and expressed as GFP-hTM5 fusion protein in CHO cells.

As shown in FIGS. 4A and C, force-expressed GFP-TC22 proteins appeared to be able to assemble onto microfilament bundles in transfected CHO cells. However, the relative amount of GFP-TC22 associated with microfilament bundles was very minimal as compared to that for force-expressed GFP-hTM5 proteins (FIG. 4E). These results suggested that TC22 isoform had a weaker affinity to actin filaments than hTM5 isoform. Both GFP-TC22 and GFP-hTM5 proteins were also found in what appeared to be the ruffle (arrowheads in FIG. 4A) and lamellipodia (FIG. 4E) regions of membrane cortex. In addition, almost every GFP-TC22 expressed cell but not GFP-hTM5 expressed cells had one or two very bright fluorescent spots in the perinuclear regions (arrows in FIG. 4A). Similar strong immunoreactive spots were also found by immunoperoxidase assay in the colon tumor tissue (see FIGS. 7A and B). Although the structure and significance of these reactive spots remained to be determined, their perinuclear nature might suggest that the expressed cells tried to degrade GFP-TC22 proteins.

Figure 5:
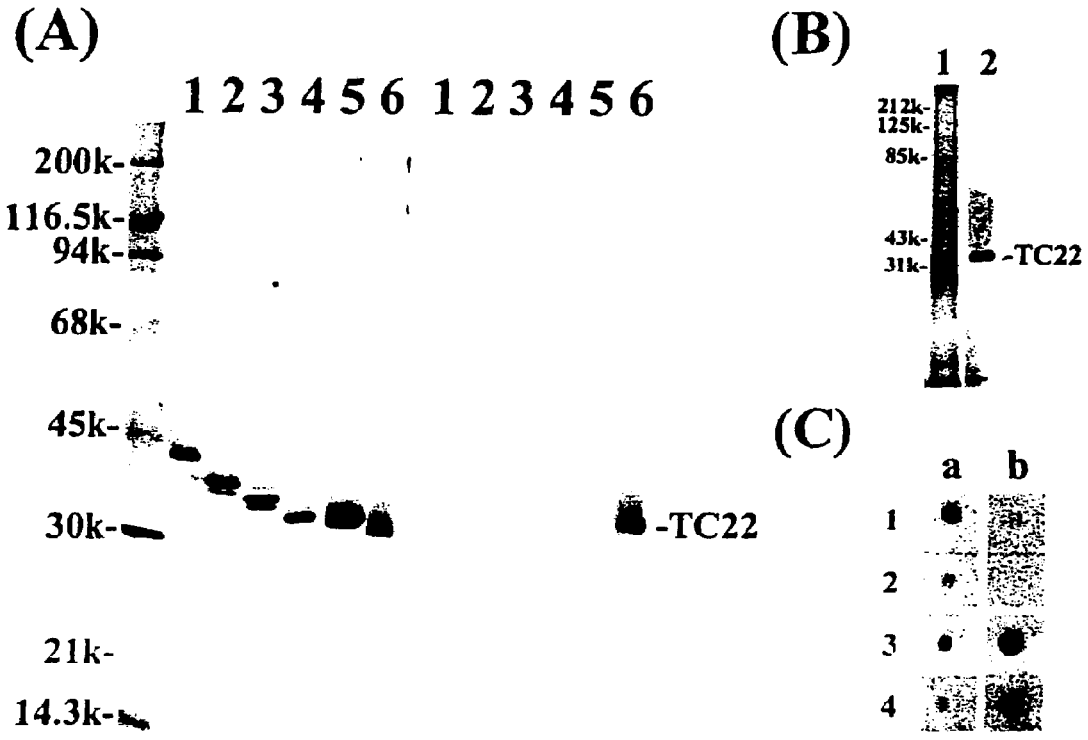
FIG. 5 presents Western blot analyses of purified recombinant human tropomyosin isoforms (A), total cell extract from a colon cancer cell line T84 (B), and different amounts of hTM5 and TC22 (C). In (A), approximately 1-2 μg of purified recombinant tropomyosin proteins, including hTM1 (lane 1), hTM2 (lane 2), hTM3 (lane 3), hTM4 (lane 4), hTM5 (lane 5) and TC22 (lane 6), were loaded in each lane and separated on 12.5% SDS-PAGE. The left panel shows the Coomassie blue-stained protein profile whereas the right panel shows the Western blot results with TC22-4 antibody. The TC22-4 antibody recognized only TC22 tropomyosin isoform. In (B), T84 total cell extract was separated on 12.5% SDS-PAGE and either stained with Coomassie blue dye (lane 1) or transferred and blotted with TC22-4 antibody (lane 2). Western blot result revealed that a protein band with molecular mass of 32 kDa was specifically recognized by TC22-4 monoclonal antibody. In (C), purified hTM5 and TC22 proteins were dotted on the membrane in two different amounts and then processed for Western blot analysis with LC1 antibody (lane a) or with TC22-4 antibody (lane b). 1 and 2, 1 μg and 0.05 μg of hTM5; 3 and 4, 1 μg and 0.05 μg of TC22.

TC22 Tropomyosin Protein is Preferentially Found in Colon Mucosa from Cancer Segments and Ulcerative Colitis To determine whether TC22 message is actually translated into protein, TC22-specific monoclonal antibodies were generated against TC22-specific peptide and used in the Western blot analysis and immunoperoxidase assay. FIG. 5 shows Western blot results on various recombinant tropomyosin isoforms and on total proteins prepared from T84 cells with monoclonal antibody TC22-4. The TC22-4 antibody recognized only TC22 isoform but not hTM1, hTM2, hTM3, hTM4, and hTM5 (right panel of FIG. 5A). A protein band with similar mobility in the gel as the recombinant TC22 was detected in the T84 protein extract with this antibody (lane 2 in FIG. 5B). The sensitivity of TC22-4 antibody to hTM5 and TC22 was further examined and compared to that of anti-hTM5 monoclonal antibody LC1 (FIG. 5C). Antibody TC22-4 was able to detect the TC22 protein as low as 0.05 μg dotted on the blot (b4 in FIG. 5C), whereas it did not cross-react with hTM5 as much as 1 μg dotted on the blot (b1 in FIG. 5C). In contrast, antibody LC1 recognized both hTM5 (a1 and a2 in FIG. 5C) and TC22 (a3 and a4 in FIG. 5C) almost equally, since the epitope for LC1 was mapped to residues 4-10 at the N-terminus of both hTM5 and TC22 (19). Therefore, the TC22-4 monoclonal antibody was further used in Western blot analysis on colon mucosa samples prepared from human individuals with various colon diseases. Of the 27 specimens, 6 were from primary colon cancer (cancer segment) and 5 from grossly normal adjacent segments of colon cancer, 9 from ulcerative colitis (UC), 2 from Crohn's disease (CD) and 5 from normal colon mucosa (spastic colon). The mean age of the patients with UC was 43 years (range 18-72 years) and the mean age for the spastic colon patients was 54 years (range 40-76 years). The two CD patients are 35 and 57 years old. The age of the colon cancer patients was not available. All patients with UC and CD were symptomatic during colonoscopic examination.

Figure 6:
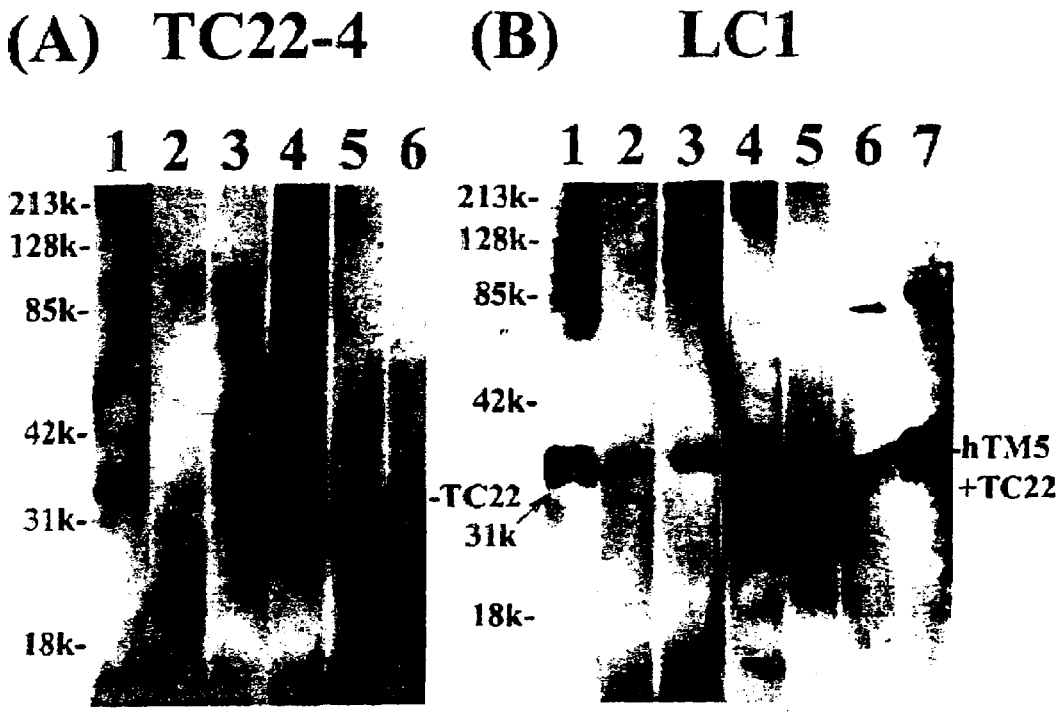
FIG. 6 presents Western blot analyses of various mucosal protein extracts with TC22-4 antibody (A) and with LC1 antibody (B). Tropomyosin-enriched fractions were prepared from colonic and jejunal mucosa, as described previously (9). Colonic mucosas were obtained from a colon cancer segment (lane 3) and its normal counterpart (lane 2), a patient with UC and sclerosing cholangitis (lane 1), and a normal colon (spastic colon syndrome) (lane 5). Jejunal mucosa was obtained from a patient who underwent gastric by-pass surgery for obesity (lane 4). Ten μg of each tropomyosin-enriched fraction were loaded per lane and used in Western blot analysis. Recombinant TC22 and hTM5 proteins were used as controls (lanes 6 and 7, respectively). The reactivity against TC22-4 is evident in the UC and the colon cancer tissue but not in the normal segment of colon cancer patient, normal colon tissue and the normal jejunum. However, LC1 reacted with each of these samples examined in parallel since hTM5 is present in all epithelial tissues. As expected, LC1 reacted with both TC22 (lane 6) and hTM5 (lane 7).
Figure 7:
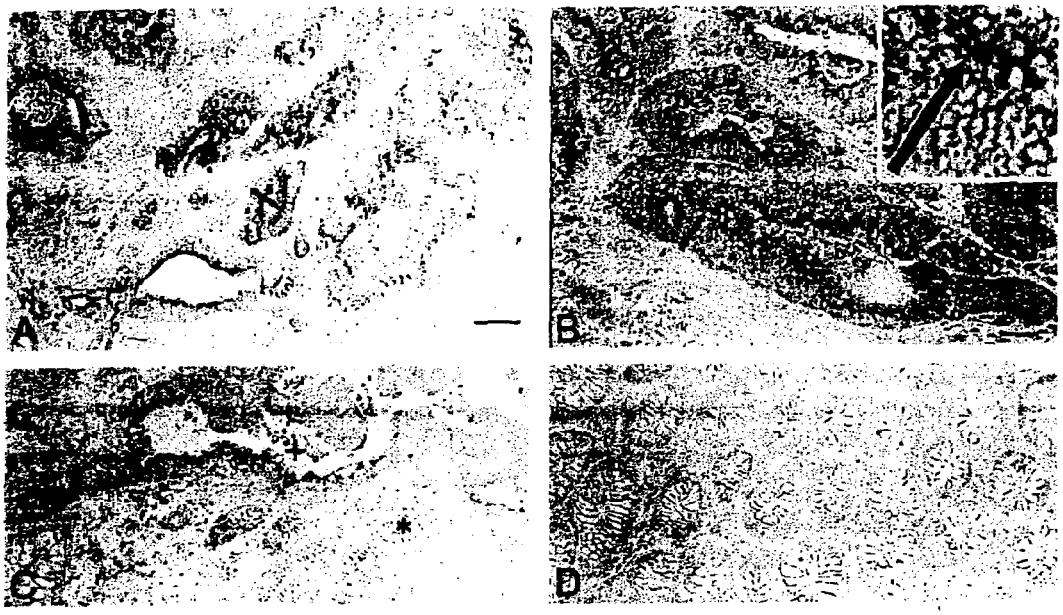
FIG. 7 presents immunoperoxidase staining of an invasive colon cancer tissue with TC22-4 monoclonal antibody. (A, and B) show lower and higher, respectively, magnifications of colon cancer tissue after staining with TC22-4. Diffuse cytoplasmic staining is clearly seen in the tumor tissue. In addition, there were strong dot-like stainings in the perinuclear areas (arrows in A and B). The inset in (B) is a 3-times higher magnification of the (B) to show the dot-like stainings. Similar dot-like staining was also seen in GFP-TC22 expressing cells, as shown in FIG. 4. Note the intervening stroma is completely non-reactive. (C) shows a cancerous gland (+) adjacent to a relatively normal gland (*). The former is immunoreactive. (D) Normal colon tissue away from the tumor area is non-reactive. Bar=200 μm for (A, C, and D); 100 μm for (B).

TC22-4 reacted with a protein band (TC22) with molecular mass of about 32 kDa and this was detected in 5 of 6 primary colon cancers (83%), 1 of 5 normal segments of colon cancer, 0 of 5 normal colon mucosa, and 0 of 2 Crohn's disease mucosa ($p<0.01$, Table 2). However, 2 of 9 UC mucosa showed the presence of TC22 isoform (Table 2). Histologically, all UC mucosa showed active disease without severe dysplasia/carcinoma. It was further noted that one of the two TC22-positive UC patients had primary sclerosing cholangitis diagnosed three years ago and the other one has been suffering from UC for 18 years. All of the other patients, with one exception, have had UC for less than 10 years, while the single patient has had UC for 14 years. FIG. 6A shows an example of such Western blot analysis on mucosal proteins from 1 colon cancer tissue (lane 3) and its adjacent normal counterpart (lane 2), colonic biopsy specimen from one of the 2 UC patients (lane 1), a normal jejunal mucosal specimen (obtained from a patient who underwent gastric bypass surgery for obesity) (lane 4) and one normal colon tissue (spastic colon, lane 5). Expression of TC22 is clearly evident in the cancer tissue, in the UC tissue, and not in the non-cancer area, normal jejunum, and normal colon tissues. Lane-6 in FIG. 6A contained recombinant TC22 protein as control. When the same protein samples at the similar concentrations were probed with antibody LC1, which recognizes both hTM5 and TC22, comparable amounts of proteins were detected in all of the tissue samples as also against recombinant hTM5 (lane 7) and TC22 (lane 6) (FIG. 6B). Further analysis of a primary colon cancer tissue by the immunoperoxidase assay using TC22-4 is shown in FIG. 7. Multiple cancerous glands invading the stromal tissue can be seen in lower magnification in FIG. 7A. The positive immunoreactivity with TC22-4 antibody was observed exclusively in malignant epithelial cells forming glands (FIGS. 7A and B), as compared to the non-reactivity on the normal colon segment from the same surgical specimen away from the cancer area (FIG. 7D). The staining in the cancer cells is diffuse and cytoplasmic. There is no reactivity in the stromal tissue in between the glands (FIGS. 7A and B). In addition, there are strong dot-like stainings in the cancer cells in the perinuclear area (arrows in FIGS. 7A and B and in the inset of FIG. 7B). FIG. 7C shows a cancerous gland with positive staining (+), adjacent to a relatively normal gland (*) with no staining.

In the present Example, a novel tropomyosin TC22 isoform from a colon cancer cell line T84 was cloned. This isoform has 5'-untranslated sequence but has most of the 5'-coding sequences identical to those in hTM5, suggesting that both isoforms are derived from the same human γ-TM gene. Furthermore, the divergent coding sequence and 3'-untranslated sequence of TC22 have high homology (96.1% and 77%, respectively) to NM-4 tropomyosin isoform from rat cochlea. Consistently, the NM-4 isoform is known to be one of rat $TM_{nm}$ or γ-TM gene products (22). However, TC22 is different from NM-4 in the internally alternative-spliced exon (exon 6); i.e., the TC22-like hTM5 utilizes a nonmuscle exon (6b) for this internal exon, whereas the rat NM-4 uses a skeletal muscle exon (6a) from γ-TM gene. The inclusion of 6a or 6b in tropomyosin isoforms has been shown to have a profound effect on their actin-binding affinity. For example, rat TM5a and TM5b are encoded from the same gene and have an identical sequence except as to exon 6. TM5b utilizes skeletal muscle-type exon 6a, while TM5a uses nonmuscle-type exon 6b. As a result of this difference, rat TM5b binds to actin filaments much stronger than TM5a does (2). Based on sequence homology and the origin of tissue, the NM-4 isoform has been speculated to be of brain or neural origin (22,23,25). It is unlikely that the TC22 isoform is of neuronal origin. Therefore, TC22 is a novel tropomyosin isoform.

Figure 4:
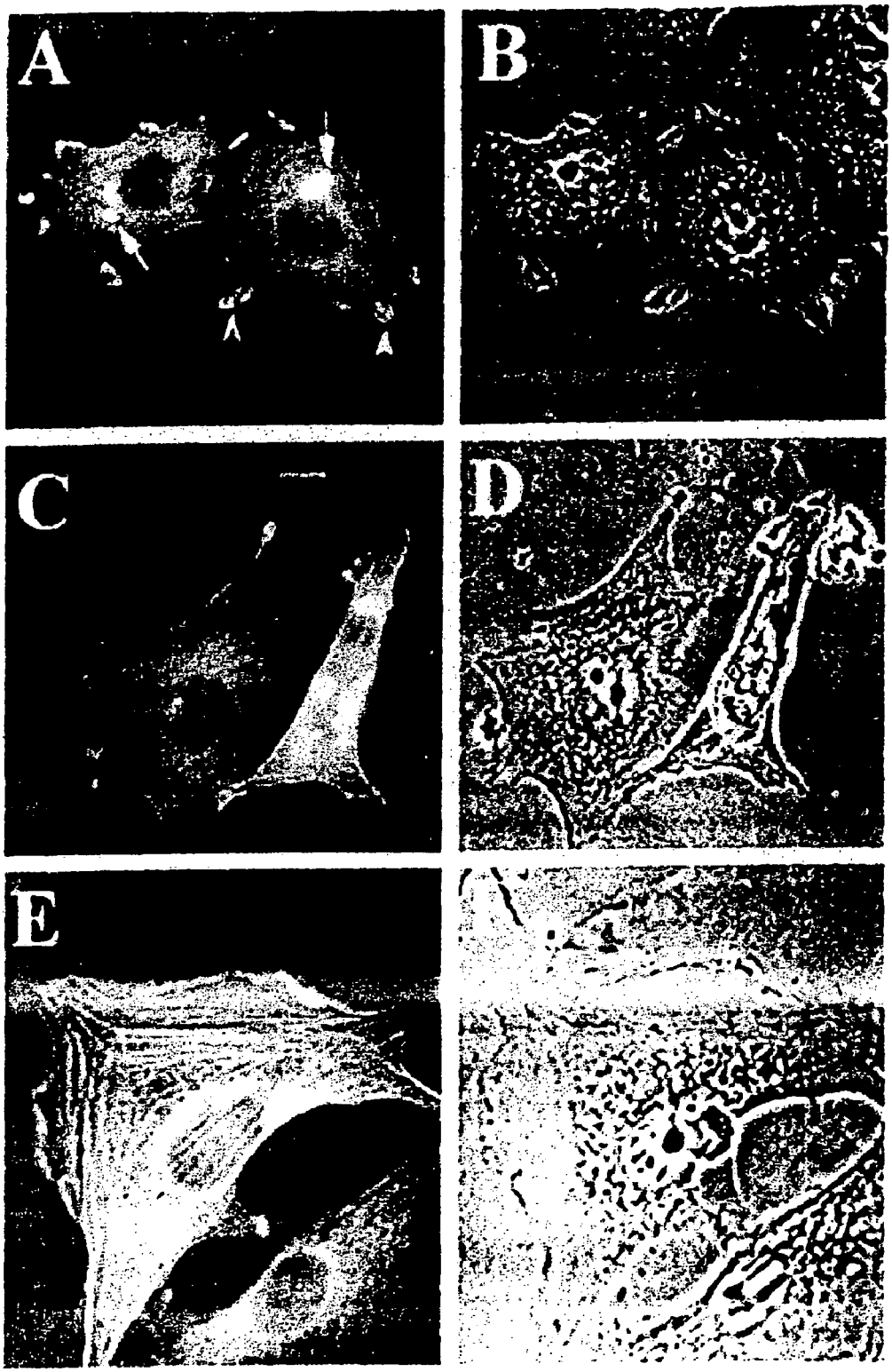
FIG. 4 presents fluorescence microscopy of transfected CHO cells expressing GFP-tropomyosin fusion proteins. CHO cells were transfected with pEGFPTC22 (A-D), expressing GFP-TC22 fusion protein, or pEGFPhTM5 (E-F), expressing GFP-hTM5 fusion protein. After selection for 1 week by growing cells in medium containing 500 μg/ml G418, resistant cells were replated and grown on coverslips for 1-2 days and then fixed for the analysis under a fluorescence microscopy. Although both GFP-tropomyosin fusion proteins are able to be assembled onto microfilament bundles, the expressed GFP-TC22 (A and C) appears to have a weaker association with actin filaments than the expressed GFP-hTM5 (E). In addition, the expressed GFP-TC22 protein is also found in one or more dots (indicated by arrows in A) at the perinuclear region. Bar, 10 μm.

TC22 protein differs from hTM5 only in the region from as #222 to the C-terminal residue. This difference likely accounts for the difference in actin binding affinity between these two isoforms, as evident that force-expressed GFP-hTM5 is more readily assembled onto actin filaments than force-expressed GFP-TC22 in CHO cells (FIG. 4). Several lines of evidence suggest that different tropomyosin isoforms have different actin binding ability (2,3,14,26-34). Tropomyosin binding to actin filaments may regulate actin activities inside the cell through stabilizing the actin filaments and/or through modulating the actin-myosin interaction. Therefore, TC22 isoform having a weak actin-binding property and an increased expression in various tumor cells may promote cancer cells in their unregulated proliferation. In contrast, a tropomyosin isoform having an excessively strong actin-binding property would cause a defect in cell division. For example, it has recently been shown that a mutant chimeric tropomyosin with unusually strong affinity to actin filaments results in an unregulated cytoplasm, leads to a defect in cytokinesis, a misalignment of mitotic spindle, and severe blebbing during cell division (17,35). Consequently, these cells expressing chimeric tropomyosin require significantly longer time for cell division (35). The weaker binding of TC22 protein to actin filaments and its preferential association with colon cancer suggest that TC22 may play a role in regulating cell proliferation.

It is intriguing that five of the six colon cancer tissues expressed TC22, suggesting that this novel hTM isoform is highly associated with colon cancer. However, further studies using large numbers of primary tumors from colon and other epithelial tissues including both benign and malignant polyps and non-epithelial malignant tumors will enhance the understanding of the stage of cell transformation at which TC22 is expressed, whether it is organ specific, and whether it is also expressed in non-epithelial tumors. Since hTM5 isoform is mainly found at the apical surface in epithelial cells of human colon (9,36), and since TC22 is likely derived from the same gene, the expression of TC22 in non-epithelial tissue is unlikely. Perhaps, a very clinically relevant observation is the presence of TC22 signal in the colonoscopic biopsy specimens from two of 9 UC patients. Interestingly, one of these two patients has primary sclerosing cholangitis (PSC), a condition associated with UC and patients with UC and PSC have been shown to have higher incidence of colon carcinoma (37,38). The second UC patient with positive TC22 reactivity was a patient who has had UC (pancolitis) for 18 years. It is well established that the incidence of colon carcinoma increases significantly with longer duration, particularly after 10 years (39). The other 7 UC patients studied had disease for a shorter duration (6 less than 10 yr and one for 14 yr). Future studies using the novel hTM isoform TC22 and the monoclonal antibody developed and disclosed herein, will facilitate the determination of whether these important tools will be clinically useful to identify high-risk patients for colon cancer in UC.

In the Western blot analysis using the TC22-specific monoclonal antibody, eighty three percent of colon cancer tissue reacted with the antibody, whereas there was no reactivity against any of the normal colonic mucosa tissue from patients with spastic colon and Crohn's disease, and also 4 out of 5 normal segments from colon cancer patients. This difference was statistically significant ($p<0.01$). The immunoperoxidase assay further localized the TC22 reactivity clearly in the cancer cells and there was no reactivity in the stroma. Normal colon epithelial cells also did not react. These results are further consistent with the Northern blot analysis data that TC22 is expressed very little, if any, in normal tissues and is elevated significantly in carcinoma tissues, including stomach, colon, and rectal cancers. In addition, we have shown that TC22 messages are also increased in fibroblasts transformed with either tumor virus for WI-38 VA 13 line or chemical carcinogen for HuT-11 line (FIG. 3A). Therefore, it appears that cell transformation to become tumor is accompanied with an unexplored mechanism to enhance alternatively splicing, which may be essential for the generation of TC22 isoform from human γ-TM gene. For example, cell transformation may turn on the expression of an unidentified splicing factor, which may be in common for all types of cancers and is required for alternatively splicing of the last exons in the γ-TM gene. Although the amount of TC22 was elevated in 5 of 6 colon cancer tissues and in 2 of 9 UC tissues (FIG. 6), the Western blot analysis using LC1 antibody recognizing both hTM5 and TC22 did not detect a significant difference between normal and tumor tissues. It has been previously shown that hTM5 is the major tropomyosin isoform present in both colon and small intestinal epithelial tissue extract (9). As one would expect, a small amount of increase in TC22 isoform may not significantly affect the total content of LC1-positive tropomyosins (hTM5 and TC22). However, the expression of the novel hTM isoform, TC22, in tumor tissues appears to be sensitive enough to encourage its use as a biomarker for early detection and for colon cancer surveillance, or perhaps to identify patients with ulcerative collitis who may be at high risk for development of carcinoma needing closer surveillance.

EXAMPLE II

Blood samples were obtained from 28 out-patients with UC and 13 patients with CD at the Crohn's and Colitis Center of New Jersey. Ten of the 13 patients with CD had colonic involvement, with or without small intestinal inflammation.

Nine healthy subjects (HS) were also included. Patient demographics, disease characteristics, and current medications are summarized in Table 1. In all subjects, the diagnosis was made according to the clinical, endoscopic, radiological, and histological criteria. During collection of blood samples, disease activity was assessed in patients with UC by the criteria of Truelove and Wins and in CD by the index of Harvey and Bradshaw. As shown in Table 1, 24 patients in the UC group and 11 patients in the CD group were symptomatic. Since all of these patients were included from the outpatient clinic, none had severe symptoms. Symptomatic patients were mostly considered mild and hence further separation between mild and moderate was not done. Four patients with UC and 2 with CD were in remission. Treatment included sulfasalazine and 5-amino salicylic acid (5-ASA) (2-4.8 g/day) in most of the patients, steroids (10-20 mg/day), and purinethol (6-mercaptopurine, 6-MP), 25-75 mg¯day, in some of the patients with UC or CD (Table 1).

Recombinant Human Tropomyosin Isoform 5 and Caldesmon

Recombinantly synthesized human tropomyosin isoform 5 and the N-terminal fragment (243 amino acid residues) from human fibroblast caldesmon, known as CaD40, were used for antigenic stimulation of peripheral blood mononuclear cells (PBMCs). The full-length complementary DNA encoding hTM5 and CaD40 was prepared from human fibroblasts. The cDNA clones were subcloned into prokaryotic expression vector pET8c. The resulting plasmids were transformed into the Escherichia coli BL21 (D3) LysS strain. Recombinant hTM5 and CaD40 were purified from bacterial lysates by ammonium sulfate fractionation, DE-52 ion-exchange chromatography, and hydroxyapatite column chromatography. The purity of hTM5 and CaD40 was examined by sodium dodecylsulfate-polyacrylamide gel electrophoresis, and the immunoreactivity was analyzed by enzyme-linked immunosorbent assay (ELISA) and transblot analysis using Isoform-specific monoclonal antibodies.

Isolation of PBMCs and Antigen-Presenting Cells

Blood samples (10 ml) were obtained from healthy subjects and UC and CD patients and used within 6 h of collection. PBMCs were purified by density centrifugation on FICOLL™ (PHARMACIA®, Uppsala, Sweden), isolated from the gradient interface, washed three times in phosphate-buffered saline (PBS, pH 7.4), and resuspended in culture medium (RPMI 1640) with 10% heat-inactivated fetal calf serum, 2 mM L-glutamine, 20 mM Hepes buffer, pH 7.4, 10 U/ml penicillin, and 100 μg/ml streptomycin sulfate. Sixty percent of the PBMCs were resuspended in cold medium (10% dimethyl sulfoxide, 90% fetal bovine serum), frozen in a liquid nitrogen freezer, and stored until used as antigen-presenting cells (APCs). Frozen PBMCs were treated with mitomycin C (SIGMA Chemical Co., St. Louis, Mo.) for 30 min at 37° C. and washed at least three times with culture medium before use.

Enzyme-Linked Immunospot Assay

An enzyme-linked immunospot (ELISPOT) assay was performed. Some modifications were made with respect to the ELISPOT assay. (FIG. 9). PBMCs from each subject (1×10' cells/well) were cultured in six replicate wells in the presence of recombinant hTM5 or medium alone. CaD40, an actin-binding protein purified in a manner similar to that of hTM5, served as a control antigen. On day 5, rIL-2 (10 Ulml) was added, and on day 7, the cells were cocultured with APCs and antigen, either hTM5 or CaD40 (second boost). A 96-well nitrocellulose plate (Millipore Co., Bedford, Mass.) was coated overnight with murine anti-human IFN-γ antibody (10 μg/ml) in 0.1 M carbonate buffer (pH 8.2) at 4° C. After the wash, each well was blocked with 1% bovine serum albumen/PBS at 37° C. for at least 1 h. On day 9, re-stimulated PBMCs (after the second boost) were added to each well in 200 μl of culture medium and incubated at 37° C. for 72 h. Subsequently, the wells were washed with 0.05% Tween-PBS at least five times, and then biotinylated mouse anti-human IFN-γ monoclonal antibody was added to each well and incubated overnight at 4° C. The next day, alkaline phosphatase-conjugated streptavidin was added to each well and incubated at room temperature for 2 h, washed, and then developed with nitroblue tetrazolium and 5-bromo-4-chloro-3-indolyl phosphate. After a wash with tap water, all of the spots (spot-forming cells, or SFC, producing IFN-γ) were counted under the zoom stereomicroscope (Olympus, New Hyde Park, N.Y.). The mean value of SFC from 6 wells containing medium only was subtracted from the mean SFC values obtained either with hTM5 or CaD40 for each patient.

Enzyme-Linked Immunosorbent Assay

PBMCs ($2\times10^5$ cells/well) were incubated with either of the antigens or with medium alone, similar to the ELISPOT assay. rIL-2 (10 U/ml) was added on day 5 and mitomycin C-treated PBMCs and antigens (0.1 μg/μl) on day 7. After culture for 5 additional days, the supernatant was collected and tested for IFN-γ using the OPTEIA™ test (PHARMINGEN™, San Diego, Calif.), a solid-phase sandwich ELISA. The detection limit of this assay was 4 pg/ml.

Statistical Analysis

All data are presented as means±SEM as well as SD. All values are compared among UC and CD individuals and healthy subjects by using the Fisher exact test. Responses against hTM5 and the control antigen CaD40 are also analyzed. Mann-Whitney statistical analysis is used to calculate the significance of spot numbers observed in antigen-stimulated samples versus medium control (no antigen). Relationships between ELISPOT data and ELISA data are analyzed with the Spearman correlation coefficient.

Results of Enzyme-Linked Immunospot Assay

T cells producing IFN-γ in response to the antigens (hTM5 and CaD40) were estimated by counting the spot-forming cells in an ELISPOT assay and also by quantitating IFN-γ secreted by T cells in an ELISA (OPTEIA™).

Figure 10:
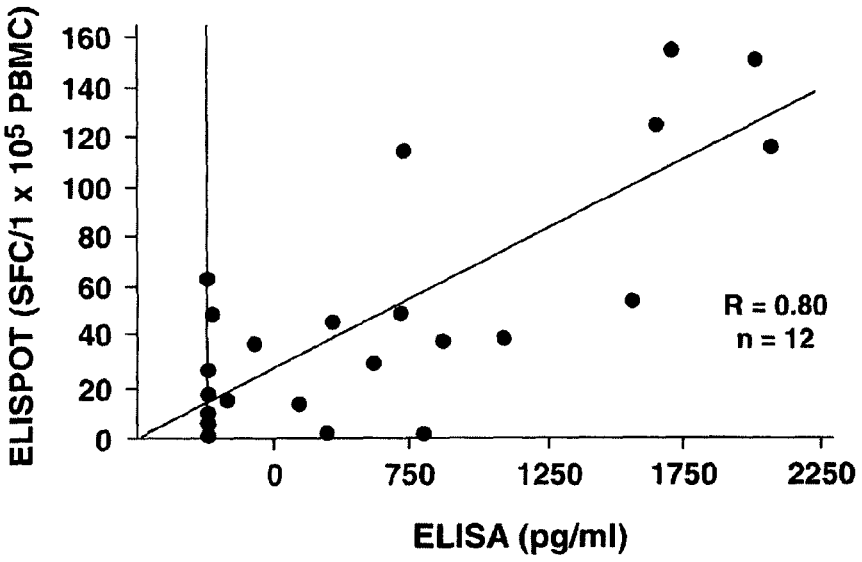
FIG. 10 illustrates the typical spots of T cells producing IFN-γ seen under a Zoom stereomicroscope with hTM5, CaD40, and medium alone (magnification, 40×).

FIG. 10 demonstrates positive spot-forming cells that secreted IFN-γ. The background SFC values (mean±SEM) in all of the three groups for patients with UC and CD and for HS with medium alone (without any antigen) were 15.4±2.2, 13.1±2.9, and 21.4±7, respectively, and these values were not significantly different among the three groups. The mean±SEM (as well as SD) SFC values in the presence of the antigens, namely hTM5 or CaD40, are shown in Table 4 and FIG. 1 1. The mean±SEM values of IFN-γ-producing SFC against hTM5 in UC, CD, and HS were 48.8±8.1, 18.6 4.6, and 20.8±8.6, respectively. The value in UC was significantly higher than CD ($P<0.005$) and HS($P<0.025$). However, there was no difference between CD and HS. The SFC values against the CaD40 antigen among the three groups were 11.6±4.6, 4.3+1.5, and 3.3±2.2, respectively. There was no statistical difference in the SFC values against the CaD40 antigen between UC and CD or UC and HS. The SFC values in UC were significantly ($P<0.05$) higher with hTM5 than with the CaD40 antigen.

Figure 11:
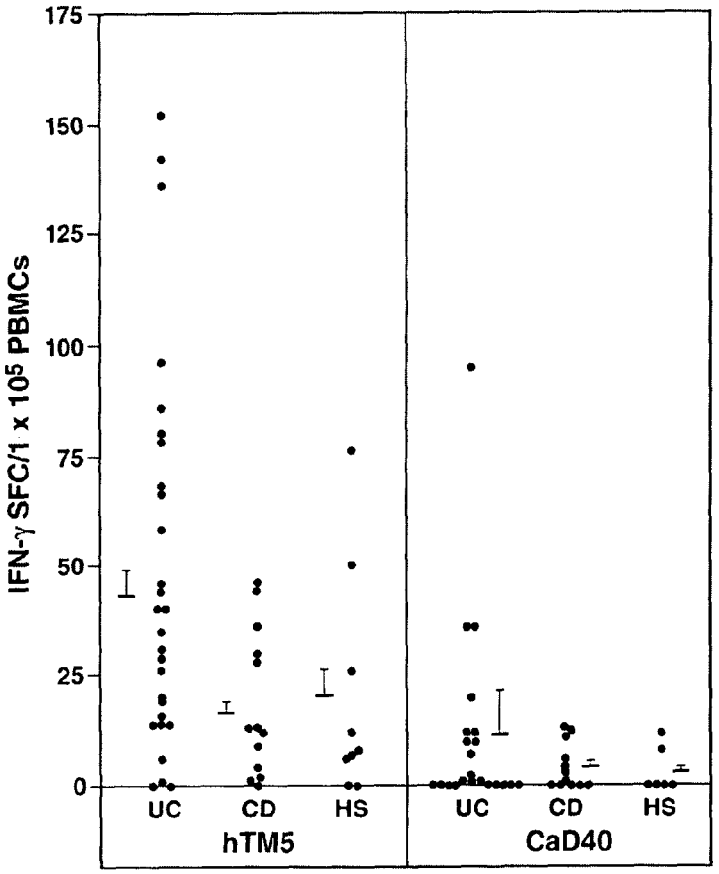
FIG. 11 is a scatterogram showing the individual values of spot forming cells producing IFN-γ with PBMCs from patients with UC or CD and HS in response to hTH5 and the control antigen, myosin-binding site of another actin binding protein, CaD40.

Among the CD patients, the highest SFC value against hTM5 in one of the 13 patients was 47 (FIG. 11). If this value is taken as a cutoff line, 10 of 28 (36%) patients with UC had SFC values higher than 47 (FIG. 11 and Table 5). Eight of these 10 patients had pancolitis. This difference in the extent of the disease with distal (rectosigmoid colon) and left-sided colitis was statistically highly significant ($P<0.01$). Eight of the 10 UC patients were symptomatic and none was treated with corticosteroids during the collection of blood samples. Five of the 10 patients were, however, treated with 6-MP (25-75 mg/day) (Table 5). A total of 4 UC patients and 4 CD patients were treated with corticosteroid. Most patients were also treated with 5-ASA compounds. Only 1 of the 9 healthy subjects had a positive response to hTM5, with an SFC value of 76 (FIG. 11). None of the 50 subjects (except 1 UC) showed any positive response against CaD40 antigen (FIG. 11).

The results demonstrate that hTM5 induced a cellular immune response, with increased IFN-γ production, in UC, but not in CD and healthy subjects. This hTM5-specific response in UC was not seen with cytoskeletal protein CaD40. All of the patients were out-patients with relatively mild symptoms of disease or in remission, and, hence, they were classified as symptomatic or in remission, thus further gradation of the disease state was not done. Among the 4 UC patients in remission, 2 were in the hTM5-positive group and 2 were in the hTM5-negative group. Age of the patients, sex, and duration did not influence the hTM5 response (Table 5). With a limited number of patients treated with corticosteroid, it appears that although statistically not significant, prednisone may have had a suppressive effect on the hTM5 response, since none of the 10 hTM5-positive UC patients was taking prednisone. However, 6-MP treatment in the dosage (25-50 mg/day) used did not influence the SFC values (Table 5).

Enzyme-Linked Immunosorbent Assay

Figure 12:
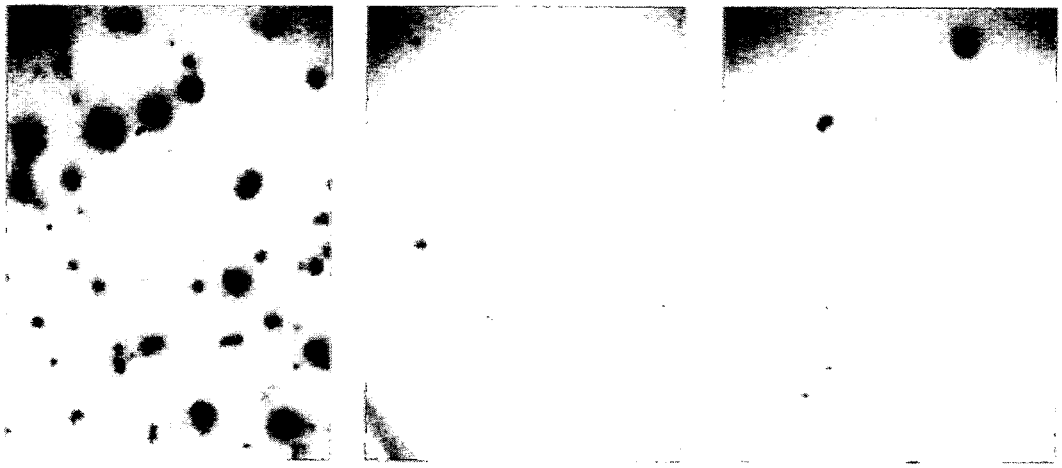
FIG. 12 shows the correlation between the ELISPOT assay to measure the spot forming cells producing IFN-γ (SFC per $1\times10^5$ PBMCs) and the ELISPOT assay to quantitate IFN-γ (pg/ml) in patients with UC (n=10) and CD (n=2).

To confirm reproducibility and accuracy of the SFC, we also measured IFN-γ levels in culture supernatant by ELISA. SFC numbers in ELISPOT assay were compared to IFN-γ levels of culture supernatant from 12 of these patients, as shown in FIG. 12. There was a significant (P<0.0001) correlation between the two methods.

Figure 3:
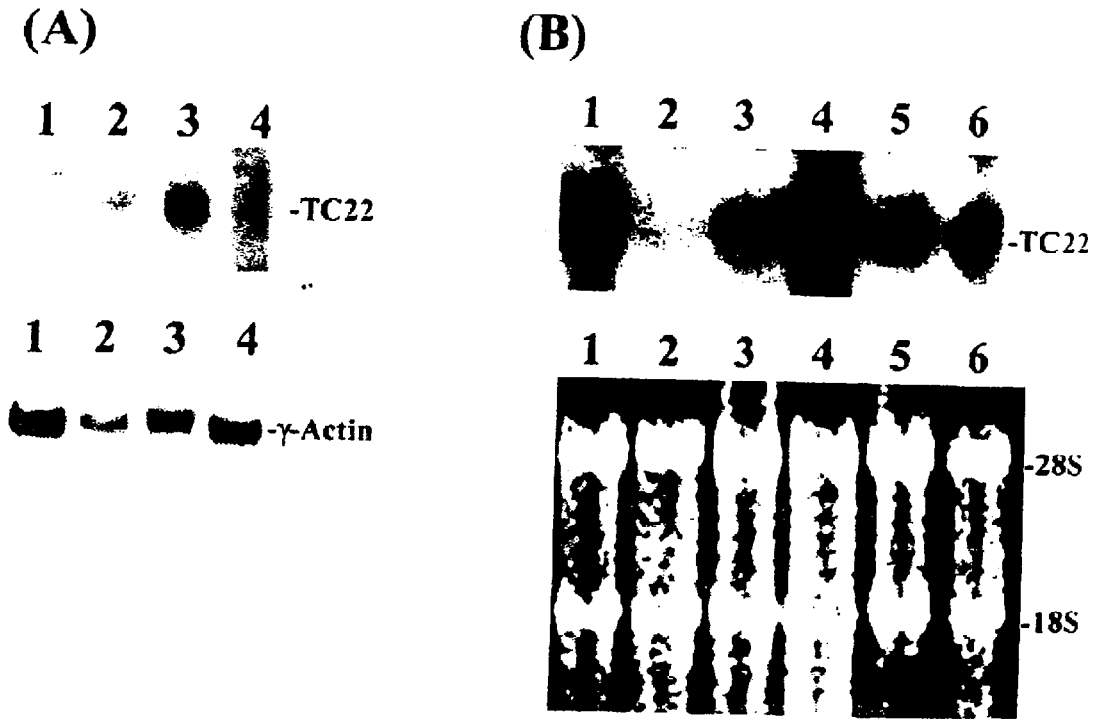
FIG. 3 presents Northern blot analyses of TC22 tropomyosin isoform expression in normal and transformed human cell lines as well as in normal and tumor tissues. (A) shows Northern blot results when TC22-specific probe (the top panel) or γ-actin control probe (the bottom panel) was used as probe on the blot membrane containing total RNA samples isolated from normal (KD and WI-38) and transformed (HuT-11 and WI-38 VA13) human cell lines. 8 μg of total RNAs were loaded in each lane. Lanes 1-4 were loaded as follows: lane 1, HuT-11; lane 2, KD; lane 3, WI-38 VA13; and lane 4, WI-38. (B) shows Northern blot results when TC22-specific probe was used as probe on the blot membrane containing total RNAs from normal and tumor tissues (the top panel). The bottom panel shows the total RNA loading as visualized by ethidium bromide staining. Lanes 1-6 were loaded as follows: lane 1, stomach tumor; lane 2, normal stomach; lane 3, colon tumor; lane 4, normal colon; lane 5, rectum tumor; lane 6, normal rectum.

This Example shows that there is a cellular immune response against hTM5 by PBMCs in patients with UC. The specific antigen-induced IFN-γ production was measured by two sensitive assays, ELISPOT and OPTEIA™. This T cell response, as evidenced by IFN-γ production, is more pronounced in patients with pancolitis. Indeed, as shown in FIG. 3, 10 of 28 (36%) patients with UC had a clear heightened response to hTM5 compared to that of each of 13 CD patients. Such a response was, however, not seen with another cytoskeletal protein, CaD40, with similar size (243 amino acid residues) as hTM5 (248 amino acids) and prepared following the same method. Navy, R. E., Lin, J. L.-C., Lin, C.-S., and Lin, J. J.-C., Human fibroblast tropomyosin isoforms: Characterization of cDNA clones and analysis of tropomyosin isoform expression in human tissues and in normal and transformed cells. CELL MOLD. CYTOSKELETON 25, 267-281, 1993. TM-related autoantibodies have been reported to be present in UC patients, but not in CD, in American patients (Geng, X., Biancone, L., Dai, H. H., Lin, J.-C., Yoshizaki, N., Dasgupta, A., Pallone, F., and Das, K. M., Tropomyosin isoforms in intestinal mucosal: Production of autoantibodies to tropomyosin isoforms in ulcerative colitis. GASTROENTEROLOGY 114, 912-922, 1998), and by two investigators involved with the initial work who performed independent studies with Italian and Japanese patients with UC and CD. Biancone, L., Monteleone, G., Marasco, R., and Pallone, F., Autoimmunity to tropomyosin isoforms in ulcerative colitis (tic) patients and unaffected relatives. CLIN. EXP. IMMUNOL. 113, 198-205, 1998; Sakamaki, S., Takayanagi, N., Yoshizaki, N., Hayashi, S., Takayama, T., Kato, J., Kogawa, K., Yamauchi, N., Takemoto, N., Nobuoka, A., Ayabe, T., Kohgo, Y., and Niitsu, Y, Autoantibodies against the specific epitope of human tropomyosin(s) detected by a peptide based enzyme immunoassay in sera of patients with ulcerative colitis show antibody dependent cell mediated cytotoxicity against HLA-DPw9 transfected L cells. GUT 47, 236-241, 2000.

Recently, we also reported that hTM5, which is the predominant hTM isoform in colon epithelial cells, is externalized specifically in colonic epithelial cells and not in small intestinal enterocytes. Using the isoform-specific monoclonal antibody, it was intriguing to demonstrate that hTM5 could be detected on the surface of colon epithelial cells by FACS analysis and in the culture supernatant as determined by ELISA and immuno-transblot analysis. Thus, hTM5, although an intracellular microfilament protein, is capable of inducing effector immune responses because of its expression on the colon epithelial cell surface and possible release from the colonocytes. In a separate study, utilizing colonoscopic biopsy specimens, we further reported that in UC, but not in CD or in controls, a large number of lamina propria B cells produced IgG against hTM5 (median values: UC, 42%; CD, 2.5%; other controls, 0%). This difference, between UC and CD and other controls, was highly significant (P<0.0001). On the basis of these observations, we studied whether hTM5 was able to induce an antigen-specific T cell response.

Previous reports showed that lamina propria T cells in healthy subjects and in inflammatory bowel diseases show diminished induction of T cell activation through the TCR/CD3 pathway, whereas the CD28/CD2 co-stimulation pathway was preserved. Therefore, we focused on peripheral blood mononuclear cells for detecting an antigen-specific T cell response against the colon epithelial protein hTM5. For the measurement of T cell activation in vitro, investigators utilized several methods, including cytokine release, surface markers, and thymidine incorporation. The ELISPOT assay is very sensitive and measures the actual number of cells secreting the specific cytokine. To increase the sensitivity and specificity, we used six replicate wells. We have also used OPTEIA™ to confirm the data from an ELISPOT assay. There was a significant (P<0.0001) correlation between the two methods.

In the preliminary experiments while establishing the ELISPOT assay, the second boost (APC+antigen) on day 7 was not included. In these experiments, SFC values, although relatively higher in UC than in CD and HS, were low (less than 20 SFC). Therefore, we performed restimulation using mitomycin-treated autologous PBMCs as APCs and the antigen (hTM5 or CaD40) to determine antigen-specific cytokine production. After restimulation, we detected significantly increased IFN-γ secretion, with hTM5 increasing the sensitivity of the assay. This restimulation on day 7 and culture for another 2 days might have increased the possibility of heightened expansion of the limited progenitor cells producing IFN-γ in response to hTM5. However, the results clearly demonstrate that hTM5 is capable of inducing a significant cellular immune response in 36% of the UC patients compared with patients with CD, suggesting that this is not a secondary phenomenon. Indeed, 10 of the 13 CD patients had symptomatic Crohn's colitis. Taken together, with significant humoral immune responses against h™, as shown by using both sera and mucosal B cells, in UC but not in CD (9-11, 23), the current example's focusing on the antigen-specific cellular immune response further add to an important autoantigenic role of hTM5 or related peptide(s) in UC. In a computer-based physicochemical analysis of the structure of 109 human autoantigens, it was observed that sequences longer than 27 residues with coiled-coil α-helices were the forerunner autoantigens for various autoimmune diseases. Among them, several sequence segments of TM were found to be the most probable autoantigen(s). Dohlman, J G , Lupas, A., and Carson, M., Long charge-rich alpha-helices in systemic autoantigens. BIOCHEM. BIOPHYS. RES. CONTINUA 195, 686-696, 1993.

IFN-γ has been a critical cytokine in several autoimmune experimental models, such as the experimental allergic encephalomyelitis model. In psoriatic patients, using PBMCs, a significant Th-1 response producing IFN-γ was found and considered to be pathogenetically important. Austin, L. M., Ozawa, M., Kikuchi, T., Walters, I. B., and Krueger, J. G., The majority of epidermal T cells in psoriasis vulgaris lesions can produce type 1 cytokines, interferon-γ, interleukin-2, and tumor necrosis factor-α, defining TC1 (cytotoxic T lymphocyte) and TH1 effector populations: A type 1 differentiation bias is also measured in circulating blood T cells in psoriasic patients. J INVEST. DERMATOL. 113, 752-759, 1999. In the current example, using PBMCs from patients with UC, we also demonstrate a Th-1 type response. IL-4 production was investigated and was similar to that in CD and HS (data not shown).

There are several reasons to explain why only 36% of UC patients showed a significant positive cellular immune response against hTM5. One factor, which was clearly shown to be important, is the extent of the disease. Eight of 12 pancolitis patients had a significantly ($P<0.01$) higher hTM5 response than with distal and/or left-sided colitis (n=16). The sensitivity of the assay to detect the antigen-specific T cells from PBMCs may be limited, the precise quantity of the antigen needed may be a factor, and there may be other autoantigenic proteins involved in UC. The positive response may also depend on the HLA haplotype of the patients, which was not examined in this study. As mentioned above, these were all outpatients, most of whom had relatively mild disease, and, hence, the frequency of hTM5-specific T cells in the peripheral blood of these patients compared to that of colonic mucosal T cells may be low. Interestingly, 2 of the patients with UC also had associated primary sclerosing cholangitis. Both of them were positive against hTM5. Indeed, 8 of 8 patients with primary sclerosing cholangitis with UC and none of the 6 primary biliary cirrhosis patients showed a significant ($P<0.05$) high humoral immune response against a specific tropomyosin peptide.

In summary, of this example, for the first time, it is demonstrated that a defined colon epithelial antigen, hTM5, is capable of inducing cellular immune response in many patients with UC. Further characterization of hTM5-specific epitope(s) involved in the T cell response, using both PBMCs and mucosal T lymphocytes from UC, may provide an important clue in the understanding of the pathophysiologic process in UC. Identification of the immunologically active hTM peptide(s) may also have therapeutic implications.

While the invention has been described and illustrated herein by references to the specific embodiments, various specific material, procedures and examples, it is understood that the invention is not restricted to the particular material combinations of material, and procedures selected for that purpose. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

TABLE 1

Primer pairs, product sizes and annealing temperatures for the PCR classification of human fibroblast tropomyosin isoforms

| TM isoform | Primer sequences | SEQ ID NO: | size (bp) | anneal-ing (° C.) |
|---|---|---|---|---|
| hTM1 | 5' AGATGTGGCCTCCCTGAACC 3' | 17 | 329 | 65 |
| | 5' GCTGTCTGGCTCGGCTCTCG 3' | 18 | | |
| hTMsmα | 5' GCACAAGGCGGAGGACAG 3' | 19 | 410 | 56 |
| | 5' TCACAGTTTTCAATTCTTC TTCAA 3' | 20 | | |

TABLE 1-continued

Primer pairs, product sizes and annealing temperatures for the PCR classification of human fibroblast tropomyosin isoforms

| TM isoform | Primer sequences | SEQ ID NO: | size (bp) | anneal-ing (° C.) |
|---|---|---|---|---|
| hTM2 | 5' CAGAGAAAAAGGCCACCG ATGCT 3' | 21 | 381 | 65 |
| | 5' TCACAGTTTTCAATTCTTC TTCAA 3' | 20 | | |
| hTM3 | 5' AAGGGCACCGAAGATGAAC TGGAC 3' | 22 | 428 | 65 |
| | 5' AGCTGTCGGACTTGGCCTT CTGAG 3' | 23 | | |
| hTM5a | 5' CCATGGCGGGTAGTAGC 3' | 24 | 495 | 56 |
| | 5' TCACAGTTTTCAATTCTTC TTCAA 3' | 20 | | |
| hTM5b | 5' CCATGGCGGGTAGTAGC 3' | 24 | 506 | 65 |
| | 5' CAAGGTCTGATCCATTATTCT 3' | 25 | | |
| hTM4 | 5' CCATGGCCGGCCTCAACTC 3' | 26 | 451 | 65 |
| | 5' GACACCTCCGCACGCTCCTCT 3' | 27 | | |
| hTM5 | 5' CCATCGAGGCGGTGAAGC 3' | 28 | 452 | 65 |
| | 5' CTCTCGGCAACGGGACTCTG 3' | 29 | | |

TABLE 2

Incidence of TC22 tropomyosin isoform in various colon mucosa specimens as detected by Western blot analysis.

| Colon mucosa derived from individuals with: | Total number of specimens examined | Number of samples positively reacted with TC22-4 | Frequency (%) |
|---|---|---|---|
| Primary colon cancer (cancer segment) | 6 | 5 | 83# |
| Primary colon cancer (normal segment) | 5 | 1 | 20 |
| Ulcerative colitis | 9 | 2* | 22 |
| Crohn's disease | 2 | 0 | 0 |
| Normal colon mucosa (spastic colon) | 5 | 0 | 0 |

#p < 0.01, colon cancer vs. normal colon mucosa or patients with inflammatory bowel disease.
*one UC patient with primary sclerosing cholangitis and the other one with a history of UC for 18 years.

TABLE 3

Demographic Data of Patients with Inflammatory Bowel Disease and Healthy Subjects

| | UC(n = 28) | CD(n = 13) | HS(n = 9) |
|---|---|---|---|
| Sex (M/F) | 19/9 | 7/6 | 5/4 |
| Age, in years (mean ± SD) | 44.6 ± 17 | 28.8 ± 14.2 | 40.3 ± 11 |
| Location of disease | 12-pancolitis<br>16-distal[a] or left-sided | 6-ileocolitis<br>4-colitis<br>3-ileitis | NA |
| Disease state | | | |
| Symptomatic | 24 | 11 | NA |
| Remission | 4 | 2 | |
| Medications[b] | | | |
| SASP/5ASA | 22 | 10 | NA |
| Corticosteroid | 4 | 4 | |
| 6-Mercaptopurine | 10 | 3 | |

Note:
UC, ulcerative colitis; CD, Crohn's disease; HS, healthy subjects; NA, not applicable
[a]Distal, proctosigmoiditis; left-sided, up to splenic flexure area.
[b]No. of patients taking various medications; SASP, azulfidine (salicyl-azo-sulfapyridine); 5-ASA, 5-aminosalicylates, 2-4.8 g/day; corticosteroid, prednisone, 10-20 mg/day; 6-mercaptopurine or azathioprine, 25-75 mg/day.

TABLE 4

IFN-γ Producing T Cell Response against hTM5 and CaD40 in Patients with UC and CD and in HS

| | No. of subjects | SFC against hTM5 (mean ± SEM) | SFC against caD40 (mean ± SEM) |
|---|---|---|---|
| UC | 28 | 48.8 ± 8.1[a] | 11.6 ± 4.6[b] |
| CD | 13 | 18.6 ± 4.6[c] | 4.3 ± 1.5[d] |
| HS | 9 | 20.8 ± 8.6[e] | 3.3 ± 2.2[f] |

Note,
Fisher exact test, a vs c, P < 0.005; a vs e, P < 0.025; c vs e, not significant; b vs d or f, not significant; d vs f, not significant. UC, ulcerative colitis; CD, Crohn's disease; HS healthy subjects.

TABLE 5 hTM5 ResDonse and Clinical Parameters of Patients with Ulcerative Colitis

| | hTM5 response | | |
|---|---|---|---|
| | Positive[a] (n = 10) | Negative (n = 18) | P value |
| Age in years (mean ± SD) | 42.4 ± 16.5 | 46.5 ± 16.9 | NS[b] |
| Sex (M/F) | 9/1 | 10/8 | NS[c] |
| Extent (pan/distal or left-sided | 8/2 | 4/14 | P < 0.01[c] |
| Duration of disease in years (mean ± SD) | 9.5 ± 9.8 | 7.5 ± 5.4 | NS[c] |
| Disease state (symptomatic/ remission) | 8/2 | 16/2 | NS[c] |
| Medications | | | |
| SASP/5-ASA (+/−) | 8/2 | 14/4 | NS[c] |
| Corticosteroid (+/−) | 0/10 | 4/14 | NS[c] |
| 6-Mercaptopurine (+/−) | 5/5 | 5/13 | NS[c] |

Note,
NS, not significant.
[a]A positive response is defined by an SFC value higher than 47, which was the highest value observed in Crohn's disease.
[b]Mann-Whitney U test.
[c]Fisher Exact Test.

REFERENCES

1. Lees-Miller JP, Helfman DM. The molecular basis for tropomyosin isoform diversity. BioEssays 1991; 13:429-437.
2. Pittenger M F, Helfman D M. In vitro and in vivo characterization of four fibroblast tropomyosins produced in bacteria: TM-2, TM-3, TM-5a and TM-5b are co-localized in interphase fibroblasts. J. Cell Biol. 1992; 118:841-858.
3. Lin J J-C, Warren K S, Wamboldt D D, Wang T, Lin J L-C. Tropomyosin isoforms in nonmuscle cells. Int. Rev. Cytol. 1997; 170:1-38.
4. Novy R E, Lin J L-C, Lin C-S, Lin J J-L. Human fibroblast tropomyosin isoforms: characterization of cDNA clones and analysis of tropomyosin isoform expression in human tissues and in normal and transformed cells. Cell Motil. Cytoskel. 1993; 25:267-281.
5. Smillie L B. Structure and functions of tropomyosin from muscle and nonmuscle sources. Trends Biochem. Sci. 1979; 4:151-155.
6. Dohlman J G, Lupas A, Carson M. Long charge-rich α-helices in systemic autoantigens. Biochim. Biophys. Res. Commun. 1993; 195:686-696.
7. Das K M, Dasgupta A, Mandal A, Geng X. Autoimmunity to cytoskeletal protein tropomyosin(s): a new clue; to the pathogenetic mechanism for ulcerative colitis. J. Immunol. 1993; 150:2487-2493.
8. Biancone L, Mandal A, Yang H, Dasgupta T, Paoluzi A O, Marcheggiano A, Paoluzi P P F, Das K M. Production of immunoglobulin G and G1 antibodies to cytoskeletal protein by lamina propria cells in ulcerative colitis. Gastroenterology 1995; 109:3-12.
9. Geng X, Biancone L, Dai H H, Lin J J-C, Yoshizaki N, Dasgupta A, Pallone F, Das K M. Tropomyosin isoforms in intestinal mucosa: production of autoantibodies to tropomyosin isoforms in ulcerative colitis. Gastroenterology 1998;114:912-922.
10. Sakamaki S, Takayanagi N, Yoshizaki N, Hayashi S, Takayama T, Kato J, Kogawa K, Yamauchi N, Takemoto N, Nobuoka A, Ayabe T, Kohgo Y, Niitsu Y. Autoantibodies against the specific epitope of human tropomyosin(s) detected by a peptide-based enzyme immunoassay in sera of patients with ulcerative colitis show antibody dependent cell mediated cytotoxicity against HLA-DPw9 transfected L-cells. Gut 2000; 47:236-241.
11. Mizoguchi A, Mizoguchi E, Chiba C, Spiekermann G M, Tonegawa S, Nagler-Anderson C, Bhan A K. Cytokine imbalance and autoantibody production in T cell receptor-α mutant mice with inflammatory bowel disease. J. Exp. Med. 1996; 183:847-856.
12. Onuma E K, Amenta P S, Ramaswamy K, Lin J J-C, Das K M. Autoimmunity in ulcerative colitis (UC): a predominant colonic mucosal B cell response against human tropomyosin isoform 5. Clin. Exp. Immunol. 2000; 121: 466-471.
13. Kesari K V, Yoshizaki N, Geng X, Lin J J-C, Das K M. Externalization of tropomyosin isoform 5 in colon epithelial cells. Clin. Exp. Immunol. 1999;118:219-227.
14. Novy R E, Sellers J R, Liu L-F, Lin J J-C. In vitro functional characterization of bacterially expressed human fibroblast tropomyosin isoforms and their chimeric mutants. Cell Motil. Cytoskel. 1993; 26:248-261.
15. Lin J J-C, Davis-Nanthakumar E J, Jin J-P, Lourim D, Novy R E, Lin J L-C. Epitope mapping of monoclonal antibodies against caldesmon and their effects on the binding of caldesmon to $Ca^{++}$/calmodulin and to actin or actin-tropomyosin filaments. Cell Motil. Cytoskel. 1991; 20:95-108.
16. Lin J J-C, Chou C-S, Lin J L-C. Monoclonal antibodies against chicken tropomyosin isoforms: Production, characterization, and application. Hybridoma 1985; 4:223-242.
17. Warren K S, Lin J J-L, McDermott JP, Lin J J-C. Forced expression of chimeric human fibroblast tropomyosin mutants affects cytokinesis. J. Cell Biol. 1995; 129:697-708.
18. Chirgwin J M, Przybyla A E:, MacDonald R J, Rutter W J. Isolation of biologically active ribonucleic acid from sources enriched in ribonuclease. Biochemistry 1979; 18:5294-5299.
19. Vera C, Sood A, Gao K-M, Yee L J, Lin J J-C, Sung L A. Tropomodulin-binding site mapped to residues 7-14 at the N-terminal heptad repeats of tropomyosin isoform 5. Arch. Biochem. Biophys. 2000; 373:16-24.
20. Das K M, Prasad I, Garla S, Amenta P. Detection of a shared colon epithelial epitope on Barrett epithelium by a novel monoclonal antibody. Ann. Intern. Med. 1994; 120: 753-756.
21. Clayton L, Reinach F C, Chumbley G M, MacLeod A R. Organization of the hTMnm gene: Implications for the evolution of muscle and non-muscle tropomyosins. J. Mol. Biol. 1988; 201:507-515.
22. Beisel K W, Kennedy J E. Identification of novel alternatively spliced isoforms of the tropomyosin-encoding gene, TMnm, in the rat cochlea. Gene 1994; 143:251-256.
23. Lees-Miller J P, Goodwin L O, Helfinan D M. Three novel brain tropomyosin isoforms are expressed from the rat α-tropomyosin gene through the use of alternative promoters and alternative RNA processing. Mol. Cell. Biol. 1990; 10:1729-1742.

24. Lemonnier M, Balvay L, Mouly V, Libri D, Fiszman M Y. The chicken gene encoding the α isoform of tropomyosin of fast-twitch muscle fibers: organization, expression and identification of the major proteins synthesized. Gene 1991; 107:229-240.
25. Had L, Faivre-Sarrailh C, Legrand C, Rabie A. The expression of tropomyosin genes in pure cultures of rat neurons, astrocytes, and oligodendrocytes is highly cell-type specific and strongly regulated during development. Mol. Brain. Res. 1993; 18:77-86.
26. Cote G P, Smillie L B. Preparation and some properties of equine platelet tropomyosin. J. Biol. Chem. 1981; 256: 7257-7261.
27. Broschat K O, Burgess D R, Low $M_r$ tropomyosin isoforms from chicken brain and intestinal epithelium have distinct actin-binding properties. J. Biol. Chem. 1986;261: 13350-13359.
28. Matsumura F, Yamashiro-Matsumura S. Purification and characterization of multiple isoforms of tropomyosin from rat cultured cells. J. Biol. Chem. 1985; 260:13851-13859.
29. Lin J J-C, Helfinan D M, Hughes S H, Chou C S. Tropomyosin isoforms in chicken embryo fibroblasts: Purification, characterization, and changes in Rous sarcoma virus-transformed cells. J. Cell Biol. 1985; 100: 692-703.
30. Lin J J-C, Hegmann T E, Lin J L-C. Differential localization of tropomyosin isoforms in cultured non-muscle cells. J. Cell Biol. 1988; 107:563-572.
31. Fanning A S, Wolenski J S, Mooseker M S, Izant J G. Differential regulation of skeletal muscle myosin II and brush border myosin I enzymology and mechanochemistry by bacterially produced tropomyosin isoforms. Cell Motil. Cytoskel. 1994; 29:29-45.
32. Pittenger M F, Kaazaz J A, Helfinan D M. Functional properties of non-muscle tropomyosin isoforms. Curr. Opin. Cell Biol. 1994; 6:96-104.
33. Pittenger M T, Kistler A, Helfman D M. Alternatively spliced exons of the OTM gene exhibit different affinities for F-actin and effects with nonmuscle caldesmon. J. Cell Sci. 1995; 108:3253-3265.
34. Temm-Grove C J, Guo W, Helfinan D M. Low molecular weight rat fibroblast tropomyosin 5 (TM5): cDNA cloning, actin-binding, localization, and coiled-coil interactions. Cell Motil. Cytoskel. 1996; 33:223-240.
35. Wong K, Wessels D, Kroll S L, Matveia A R, Lin J L-C, Soll D R, Lin J J-C. Forced expression of a dominant-negative chimeric tropomyosin causes abnormal motile behavior during cell division. Cell Motil. Cytoskel. 2000; 45:121-132.
36. Percival J M, Thomas G, Cock T-A, Gardiner E M, Jeffrey P L, Lin J J-C, Weinberger R P, Gunning P. Sorting of tropomyosin isoforms in synchronized NIH 3T3 fibroblasts: Evidence for distinct microfilament populations. Cell Motil. Cytoskel. 2000; 47:189-208.
37. Broome U, Lofberg R, Veress R, Eriksson L S. Primary sclerosing cholangitis and ulcerative colitis: indicator of increased neoplastic potential. Hepatology 1995; 22:1404-1408.
38. Brentnall T A, Haggitt R C, Rabinovitch P S, Kimmey M B, Bonner M P, Levine D S, Kowdley K V, Stevens A C, Crispin D A, Emond M, Rubin C E. Risk and natural history of colonic neoplasia in patients with primary sclerosing cholangitis and ulcerative colitis. Gastroenterology 1996;110:331-338.
39. Collins R H J, Feldman M, Fordtran J S. Colon cancer dysplasia and surveillance in patients with ulcerative colitis: a critical review. New Engl. J. Med. 1987; 316: 1654-1658.
40. MacLeod A R, Houlker C, Reinach F C, Talbot K. The mRNA and RNA copy pseudogenes encoding $TM^{30}_{nm}$, a human cytoskeletal tropomyosin. Nucleic Acids Res. 1986; 14:8413-8426.
41. MacLeod A R, Talbot K, Smillie L B, Houlker C. Characterization of a cDNA defining a gene family encoding $TM30_{p1}$, a human fibroblast tropomyosin. J. Mol. Biol. 1987; 194:1-10.
42. MacLeod A R, Houlker C, Reinach F C, Smillie L B, Talbot K, Modi G, Walsh F S. A muscle-type tropomyosin in human fibroblasts: Evidence for expression by an alternative RNA splicing mechanism. Proc. Natl. Acad. Sci. USA 1985; 82:7835-7839.
43. Talbot K, MacLeod A R. Novel form of nonmuscle tropomyosin in human fibroblast. J. Mol. Biol. 1983; 164: 159-174.
44. Lin C S, Leavitt J. Cloning and characterization of a cDNA encoding transformation-sensitive tropomyosin isoform 3 from tumorigenic human fibroblasts. Mol. Cell. Biol. 1988; 8:160-168.
45. MacLeod A R, Gooding C. Human hTMa gene: Expression in muscle and nonmuscle tissue. Mol. Cell. Biol. 1988; 8:433-400.
46. Brandtzaeg, P., Autoimmunity and ulcerative colitis: Can two enigmas make sense together? Gastroenterology 109, 307-312, 1995.
47. Targan, S. R., Landers, C. J., Cobb, L., MacDermott, R. P., and Vidrich, A., Perinuclear anti-neutrophil cytoplasmic antibodies are spontaneously produced by mucosal B cells in ulcerative colitis patients. J. Immunol. 155, 3262-3267, 1995.
48. Olsson, Y K., Wang, W.-Z., Xiao, B.-G., Kostulas, V., Jiang, Y.-P., Andersson, G., Erke, H.-P., and Link, H., Autoreactive T lymphocytes in multiple sclerosis determined by antigen-induced secretion of interferon-γ. J. Clin. Invest. 86, 981-985, 1990.
49. Atkinson, M. A., and Maclaren, N. K., The pathogenesis of insulin-dependent diabetes mellitus. N. Engl. J. Med. 331, 1428-1436, 1994.
50. Ben-Nun, A., Wekerle, H., and Cohen, I.R., The rapid isolation of clonable antigen-specific T-lymphocyte lines capable of mediating autoimmune encephalomyelitis. Eur. J. Immunol. 11, 195199, 1981.
51. Fuss, L, Neurath, M. F., Kelsall, B. L., Stuber, E., and Strober, W., Antibodies to interleukin 12 abrogate established experimental colitis in mice. J. Exp. Med 182, 1281-1290, 1995.
52. Das, K. M., Dasgupta, A., Mandel, A., and Geng, X., Autoimmunity to cytoskeletal protein tropomyosin(s): A clue to the pathogenetic mechanism for ulcerative colitis. J. Immunol. 150, 24872493, 1993.
53. Biancone, L., Mandal, A., Yang, H., Dasgupta, T., Paoluzi, A. O., Marcheggiano, A., Paoluzi, P., Pallone, F., and Das, K. M., Production of immunoglobulin G and G1 antibodies to cytoskeletal protein by lamina propria cells in ulcerative colitis. Gastroenterology 109, 3-12, 1995.
54. Geng, X., Biancone, L., Dai, H. H., Lin, J.-C., Yoshizaki, N., Dasgupta, A., Pallone, F., and Das, K. M., Tropomyosin isoforms in intestinal mucosa: Production of autoantibodies to tropomyosin isoforms in ulcerative colitis. Gastroenterology 114, 912-922, 1998.

55. Biancone, L., Monteleone, G., Marasco, R., and Pallone, F., Autoimmunity to tropomyosin isoforms in ulcerative colitis (tic) patients and unaffected relatives. Clin. Exp. Immunol. 113, 198-205,1998.
56. Sakamaki, S., Takayanagi, N., Yoshizaki, N., Hayashi, S., Takayama, T., Kato, J., Kogawa, K., Yamauchi, N., Takemoto, N., Nobuoka, A., Ayabe, T., Kohgo, Y., and Niitsu, Y., Autoantibodies against the specific epitope of human tropomyosin(s) detected by patients with ulcerative colitis show antibody dependent cell mediated cytotoxicity against HLA=DPw9 transfected L cells. Gut 47, 236-241, 2000.
57. Lin, J. J., Warren, K. S., and Wamboldt, D. D., Tropomyosin isoforms in nonmuscle cells. Int. Reo. Cytol. 170, 1-38, 1997.
58. Mizoguchi, A., Mizoguchi, E., Chiba, C., Spiekermann, G. M., Tonegawa, S., Nagler-Anderson, C., and Bhan, A. K., Cytokine imbalance and autoantibody production in T cell receptor-α mutant mice with inflammatory bowel disease. J. Exp. Med. 183, 847-856, 1996.
59. Mizoguchi, A., Mizoguchi, E., Chiba, C., and Bhan, A. K., Role of appendix in the development of inflammatory bowel disease in TCR-α mutant mice. J. Exp. Med. 184, 707-715, 1996.
60. Solomon, P., Pizzimenti, A., Panja, A., Reisman, A., and Mayer, L., The expression and regulation of class II antigens in normal and inflammatory bowel disease peripheral blood monocytes and intestinal epithelium. Autoimmunity 9, 141-149, 1991.
61. Breese, E., Braegger, C. P., Corrigan, C. J., Walker-Smith, J. A., and MacDonald, T. T., Interleukin-2 and interferon gamma-secreting T cells in normal and diseased human intestinal mucosa. Immunology 78, 127-131, 1993.
62. Truelove, S. C., and Witts, L. J., Cortisone in ulcerative colitis: Final report on a therapeutic trial. BMJ2, 1041-1048, 1955.
63. Harvey, R. F., and Bradshaw, J. M., A simple index of Crohn's disease activity. Lancet 8, 514, 1980.
64. Navy, R. E., Lin, J. L.-C., Lin, C.-S., and Lin, J. J.-C., Human fibroblast tropomyosin isoforms: Characterization of cDNA clones and analysis of tropomyosin isoform expression in human tissues and in normal and transformed cells. Cell Mold. Cytoskeleton 25(3), 267-281, 1993.
65. Czerkinsky, C., Andersson, G., Erke, H. P., Nilsson, L. A., Klareskog, L., and Ouchterlony, O., Reverse ELISPOT assay for clonal analysis of cytokine production: Enumeration of gammainterferon-secreting cells. J Immunol. Methods 110, 29-36, 1988.
66. McCutcheon, M., Wehner, N., Wensky, A., Kushner, M., Doan S., Hsiao, L., Calabresi, P., Ha, T., Tran, T. V., Tate, K. M., Winkelhake, J., and Spack, E. G., A sensitive ELISPOT assay to detect low-frequency human T lymphocytes. J. Immunol. Methods 210, 149-166, 1997.
67. Kesari, K. V., Yoshizaki, N., Geng, X., Lin, J.-C., and Das, K. M., Externalization of tropomyosin isoform 5 in colon epithelial cells. Clin. Exp. Immunol. 118, 219-227, 1999.
68. Onuma, E. K., Amenta, P. S., Ramaswamy, K., Lin, J. J.-C., and Das, K. M., Autoimmunity in ulcerative colitis (UC): A predominant colonic mucosal B cell response against human tropomyosin isoform 5. Clin. Exp. Immunol. 121, 466-471, 2000.
69. Ebert, E. C., Proliferative responses of human intraepithelial lymphocytes to various T-cell stimuli. Gastroenterology 97, 1372-1381, 1989.
70. Qiao, L., Schurmann, G., Betzler, M., and Meuer, S. C., Activation and signaling status of human lamina propria T lymphocytes. Gastroenterology 101, 1529-1536, 1991.
71. Fuss, I. J., Neurath, M., Boirivant, M., Klein, J. S., DeLa Motte, C., Strong, S. A., Fiocchi, C., and Strober, W., Disparate $CD4^+$ lamina propria (LP) lymphokine secretion profiles in inflammatory bowel disease: Crohn's disease LP cells manifest increased secretion of IFN-gamma, whereas ulcerative colitis LP cells manifest increased secretion of IL-5. J. Immunol. 157, 1261-1270, 1996.
72. Jung, T., Schauer, U., Heusser, C., Neuman, C., and Rieger, C., Detection of intracellular cytokines by flow cytometry. J Immunol. Methods 159, 197-207, 1993.
73. Maine, V. C., Suni, M. A., and Ruitenberg, J. J., Rapid flow cytometric method for measuring lymphocyte subset activation. Cytometry 20, 127-133, 1995.
74. Plebanski, M., and Burtles, S. S., In vitro primary responses of human T cells to soluble protein antigens. J. Immunol. Methods 170, 15-25, 1994.
75. Dohlman, J. G., Lupas, A., and Carson, M., Long charge-rich alpha-helices in systemic autoantigens. Biochem. Biophys. Res. Continua. 195, 686-696, 1993.
76. Vashishtha, A., and Fischetti, V. A., Surface-exposed conserved region of the streptococcal M protein induces antibodies crossreactive with denatured forms of myosin. J. Immunol. 150, 4693-4701, 1993.
77. Duchmann, R., May, E., Heike, M., Knolle, P., Neurath, M., and Meyer zum Buschenfelde, K.-H., T cell specificity and cross reactivity towards enterobacteria, bacteroides, bifidobacterium, and antigens from resident intestinal flora in humans. Gut 44, 812-818, 1999.
78. Cohavy, O., Bruckner, D., Gordon, L. K., Misra, R., Wei, B., Eggena, M. E., Targan, S. R., and Braun, J., colonic bacteria express an ulcerative colitis pANCA-related protein epitope. Infect. Immun. 68, 1542-1548, 2000.
79. Ando, D. G., Clayton, J., Kono, D., Urban, J. L., and Sercarz, E. E., Encephalitogenic T cells in the B10.PL model of experimental allergic encephalomyelitis (EAE) are of the Th-1 lymphokine subtype. Cell. Immunol. 124, 132-143, 1989.
80. Austin, L. M., Ozawa, M., Kikuchi, T., Walters, I. B., and Krueger, J. G., The majority of epidermal T cells in psoriasis vulgaris lesions can produce type 1 cytokines, interferon-γ, interleukin-2, and tumor necrosis factor-α, defining TC1 (cytotoxic T lymphocyte) and TH1 effector populations: A type 1 differentiation bias is also measured in circulating blood T cells in psoriasic patients. J Invest. Dermatol. 113, 752-759, 1999.
81. Inoue, N., Watanabe, M., Sato, T., Okazawa, A., Yamazaki, M., Kanai, T., Ogata, H., Iwao, Y, Ishii, H., and Hibi, T., Restricted $V_H$ gene usage in lamina propria B cells producing anticolon antibody from patients with ulcerative colitis. Gastroenterology 121, 15-23, 2001.

SEQUENCE LISTING

```
<160> NUMBER OF SEQ ID NOS: 29

<210> SEQ ID NO 1
<211> LENGTH: 26
<212> TYPE: PRT
<213> ORGANISM: Homo sapiens
```

<400> SEQUENCE: 1

Glu Arg Leu Tyr Ser Gln Leu Glu Arg Asn Arg Leu Leu Ser Asn Glu
1 5 10 15

Leu Lys Leu Thr Leu His Asp Leu Cys Asp
20 25

<210> SEQ ID NO 2
<211> LENGTH: 247
<212> TYPE: PRT
<213> ORGANISM: Homo sapiens

<400> SEQUENCE: 2

Met Ala Gly Ile Thr Thr Ile Glu Ala Val Lys Arg Lys Ile Gln Val
1 5 10 15

Leu Gln Gln Gln Ala Asp Asp Ala Glu Glu Arg Ala Glu Arg Leu Gln
20 25 30

Arg Glu Val Glu Gly Glu Arg Arg Ala Arg Glu Gln Ala Glu Ala Glu
35 40 45

Val Ala Ser Leu Asn Arg Arg Ile Gln Leu Val Glu Glu Glu Leu Asp
50 55 60

Arg Ala Gln Glu Arg Leu Ala Thr Ala Leu Gln Lys Leu Glu Glu Ala
65 70 75 80

Glu Lys Ala Ala Asp Glu Ser Glu Arg Gly Met Lys Val Ile Glu Asn
85 90 95

Arg Ala Leu Lys Asp Glu Glu Lys Met Glu Leu Gln Glu Ile Gln Leu
100 105 110

Lys Glu Ala Lys His Ile Ala Glu Glu Ala Asp Arg Lys Tyr Glu Glu
115 120 125

Val Ala Arg Lys Leu Val Ile Ile Glu Gly Asp Leu Glu Arg Thr Glu
130 135 140

Glu Arg Ala Glu Leu Ala Glu Ser Arg Cys Arg Glu Met Asp Glu Gln
145 150 155 160

Ile Arg Leu Met Asp Gln Asn Leu Lys Cys Leu Ser Ala Ala Glu Glu
165 170 175

Lys Tyr Ser Gln Lys Glu Asp Lys Tyr Glu Glu Glu Ile Lys Ile Leu
180 185 190

Thr Asp Lys Leu Lys Glu Ala Glu Thr Arg Ala Glu Phe Ala Glu Arg
195 200 205

Ser Val Ala Lys Leu Glu Lys Thr Ile Asp Asp Leu Glu Glu Arg Leu
210 215 220

Tyr Ser Gln Leu Glu Arg Asn Arg Leu Leu Ser Asn Glu Leu Lys Leu
225 230 235 240

Thr Leu His Asp Leu Cys Asp
245

<210> SEQ ID NO 3
<211> LENGTH: 1131
<212> TYPE: DNA
<213> ORGANISM: Homo sapiens

<400> SEQUENCE: 3 gggtgggcac catggctggg atcaccacca tcgaggcggt gaagcgcaag atccaggttc 60 tgcagcagca ggcagatgat gcagaggagc gagctgagcg cctccagcga gaagttgagg 120 gagaaaggcg ggcccgggaa caggctgagg ctgaggtggc ctccttgaac cgtaggatcc 180 agctggttga agaagagctg gaccgtgctc aggagcgcct ggccactgcc ctgcaaaagc 240

```
tggaagaagc tgaaaaagct gctgatgaga gtgagagagg tatgaaggtt attgaaaacc    300

gggccttaaa agatgaagaa aagatggaac tccaggaaat ccaactcaaa gaagctaagc    360

acattgcaga agaggcagat aggaagtatg aagaggtggc tcgtaagttg gtgatcattg    420

aaggagactt ggaacgcaca gaggaacgag ctgagctggc agagtcccgt tgccgagaga    480

tggatgagca gattagactg atggaccaga acctgaagtg tctgagtgct gctgaagaaa    540

agtactctca aaaagaagat aaatatgagg aagaaatcaa gattcttact gataaactca    600

aggaggcaga gacccgtgct gagtttgctg agagatcggt agccaagctg gaaaagacaa    660

ttgatgacct ggaagagcgt ctctacagcc aacttgagcg aaaccgcctg ctttctaatg    720

agctgaagct aacgctgcat gatctgtgtg actgatgggc agggctcaat gatgcccatt    780

aaactgagct tactgctcac accactgacc tggaccccaa caaaaagctg attgtctttt    840

taaaagttat tattttagcc ctgagcaaat tgcattttaa ttggggcagt tagaatgttg    900

atttcctaac agcattgtga agttgaccat tgtgaagttt ctgtccttta gaagagatta    960

tgggtgaaga agggaggggc ctgagagatt atagtgagaa aacttgcgag aattttgttt   1020

tccaccctta tttgctgctc tttcacttgg gcactgactg taggatatgt tcccttgcat   1080

ggatgttttt aacaataaaa ggactgactt gaaaaaaaaa aaaaaaaaaa a            1131
```

<210> SEQ ID NO 4
<211> LENGTH: 27
<212> TYPE: PRT
<213> ORGANISM: Homo sapients

<400> SEQUENCE: 4

```
Asp Lys Leu Lys Cys Thr Lys Glu Glu His Leu Cys Thr Gln Arg Met
1               5                   10                  15

Leu Asp Gln Thr Leu Leu Asp Leu Asn Glu Met
            20                  25
```

<210> SEQ ID NO 5
<211> LENGTH: 27
<212> TYPE: PRT
<213> ORGANISM: Homo sapiens

<400> SEQUENCE: 5

```
Glu Lys Leu Ala Gln Ala Lys Glu Glu Asn Val Gly Leu His Gln Thr
1               5                   10                  15

Leu Asp Gln Thr Leu Asn Glu Leu Asn Cys Ile
            20                  25
```

<210> SEQ ID NO 6
<211> LENGTH: 27
<212> TYPE: PRT
<213> ORGANISM: Homo sapiens

<400> SEQUENCE: 6

```
Glu Lys Val Ala His Ala Lys Glu Glu Asn Leu Ser Met His Gln Met
1               5                   10                  15

Leu Asp Gln Thr Leu Leu Glu Leu Asn Asn Met
            20                  25
```

<210> SEQ ID NO 7
<211> LENGTH: 27
<212> TYPE: PRT
<213> ORGANISM: Homo sapiens

<400> SEQUENCE: 7

Glu Thr Leu Ala Ser Ala Lys Glu Glu Asn Val Glu Ile His Gln Thr
1 5 10 15

Leu Asp Gln Thr Leu Leu Glu Leu Asn Asn Leu
20 25

<210> SEQ ID NO 8
<211> LENGTH: 26
<212> TYPE: PRT
<213> ORGANISM: Rattus sp.

<400> SEQUENCE: 8

Glu Arg Leu Tyr Ser Gln Leu Glu Arg Asn Arg Leu Leu Ser Asn Glu
1 5 10 15

Leu Lys Leu Thr Leu His Gly Leu Cys Asp
20 25

<210> SEQ ID NO 9
<211> LENGTH: 24
<212> TYPE: PRT
<213> ORGANISM: Rattus sp.

<400> SEQUENCE: 9

Asp Gln Leu Tyr His Gln Leu Glu Gln Asn Arg Arg Leu Thr Asn Glu
1 5 10 15

Leu Lys Leu Ala Leu Asn Glu Asp
20

<210> SEQ ID NO 10
<211> LENGTH: 24
<212> TYPE: PRT
<213> ORGANISM: Gallus sp.

<400> SEQUENCE: 10

Asp Gln Leu Tyr Gln Gln Leu Glu Gln Asn Ser Arg Leu Thr Asn Glu
1 5 10 15

Leu Lys Leu Ala Leu Asn Glu Asp
20

<210> SEQ ID NO 11
<211> LENGTH: 26
<212> TYPE: PRT
<213> ORGANISM: Leishmania major

<400> SEQUENCE: 11

Arg Arg Leu Ser Ser Gln Leu Glu Thr Gln Lys Thr Leu Val Asn Asp
1 5 10 15

Leu Phe Val Val Leu His Asp Val Cys Arg
20 25

<210> SEQ ID NO 12
<211> LENGTH: 356
<212> TYPE: DNA
<213> ORGANISM: Homo sapiens

<400> SEQUENCE: 12 tgggcagggc tcaatgatgc ccattaaact gagcttactg ctcacaccac tgacctggac 60 cccaacaaaa agctgattgt ctttttaaaa gttattattt tagccctgag caaattgcat 120 tttaattggg gcagttagaa tgttgatttc ctaacagcat tgtgaagttg accattgtga 180 agtttctgtc ctttagaaga gattatgggt gaagaaggga ggggcctgag agattatagt 240 gagaaaactt gcgagaattt tgttttccac ccttatttgc tgctctttca cttgggcact 300 gactgtagga tatgttccct tgcatggatg tttttaacaa taaaaggact gacttg 356

<210> SEQ ID NO 13
<211> LENGTH: 316
<212> TYPE: DNA
<213> ORGANISM: Rattus sp.

<400> SEQUENCE: 13 cgggccgggc tccctgatgc ccagtaaacc cacaccactg acctggaccc agccaaaagc 60 tgactgcctt ttaaaaagtc actgttcgcc ctaagcaagt tgctttttaa tgagggcagc 120 tagactactg ttgatttcct ggcagccccc ttcaagttgc aatggctatt tctattctag 180 aagagattgt gggtgatgaa gatggggcct gggaggttta gtgcagaact tgaaaaccgt 240 tagctgcagc cctctcacct gtatactgac tgtagggttt gctcacctgc atggttattt 300 tctaacaata aaaaca 316

<210> SEQ ID NO 14
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 14 gtcgaattca tggctgggat caccac 26

<210> SEQ ID NO 15
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 15 ggtggatcct cagtcacaca gatcatgc 28

<210> SEQ ID NO 16
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 16 ggtggatcct acatctcatt ccaggtcaag 30

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 17 agatgtggcc tccctgaacc 20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 18 gctgtctggc tcggctctcg 20

<210> SEQ ID NO 19
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 19 gcacaaggcg gaggacag 18

<210> SEQ ID NO 20
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 20 tcacagtttt caattcttct tcaa 24

<210> SEQ ID NO 21
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 21 cagagaaaaa ggccaccgat gct 23

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 22 aagggcaccg aagatgaact ggac 24

<210> SEQ ID NO 23
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 23 agctgtcgga cttggccttc tgag 24

<210> SEQ ID NO 24
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 24 ccatggcggg tagtagc 17

-continued

```
<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 25

caaggtctga tccattattc t                                              21


<210> SEQ ID NO 26
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 26

ccatggccgg cctcaactc                                                 19


<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 27

gacacctccg cacgctcctc t                                              21


<210> SEQ ID NO 28
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 28

ccatcgaggc ggtgaagc                                                  18


<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 29

ctctcggcaa cgggactctg                                                20
```

What is claimed is:

1. An isolated tropomyosin isoform (TI) protein, the isoform identified as TC22, consisting of the amino acid sequence set forth in SEQ ID NO:2.

2. An isolated tropomyosin isoform (TI) protein fragment consisting of the amino acid sequence set forth in SEQ ID NO:1.

3. A labeled TI protein fragment wherein the TI protein fragment of claim 2 is labeled.

4. A composition comprising the TI protein of claim 1.

5. A composition comprising the TI protein fragment of claim 2.

*6. A molecular complex comprising either the tropomyosin isoform (TI) protein consisting of the amino acid sequence set forth in the SEQ ID NO: 2 or the TI protein fragment consisting of the amino acid sequence set forth in SEQ ID NO: 1 and a binding molecule comprising at least a Fab, Fab', $F(ab')_2$ or F(v) portion of an antibody, wherein said antibody portion binds to the amino acid sequence set forth in SEQ ID NO:1 and wherein said complex is formed by immunoreacting said tropomyosin isoform and said binding molecule.*

*7. The molecular complex of claim 6, further comprising a detectable labeling component wherein detection of said molecular complex is an indicator of a dysfunction associated with the alimentary canal and/or the epithelium thereof.*

*8. The molecular complex of claim 6, wherein said tropomyosin isoform protein is obtained from a biological sample from alimentary canal tissue or body fluids selected from the group consisting of peripheral blood, serum, urine, and stool.*

*9. The molecular complex of claim 7, wherein said labeling is selected from the group consisting of an enzyme, a fluoro-*

*phore, a chromophore, a radioisotope, a dye, colloidal gold, latex particles and chemiluminescent agents.*

*10. The molecular complex of claim 6, wherein said binding molecule is formed from a test kit comprising a predetermined amount of a label selected from the group consisting of an enzyme, a fluorophore, a chromophore, a radioisotope, a dye, colloidal gold, latex particles and chemiluminescent agents and a binding molecule which immunoreacts with a targeting partner having the amino acid sequence set forth in SEQ ID NO: 1 or SEQ ID NO: 2; and directions for use of said kit.*

*11. The molecular complex of claim 10, wherein the amino acid sequence in the test kit is SEQ ID NO: 2.*

*12. The molecular complex of claim 6, wherein said binding molecule is the binding site of an antibody selected from the group consisting of polyclonal antibodies, monoclonal antibodies, and chimeric bispecific antibodies.*

*13. The molecular complex of claim 12, wherein said antibodies are monoclonal antibodies.*

*14. The molecular complex of claim 6, prepared by a method for testing a mammalian subject for dysfunction of the alimentary canal or the epithelium thereof associated with the expression of a tropomyosin isoform (TI) protein identified as TC22, consisting of the amino acid sequence set forth in SEQ ID NO: 1 or SEQ ID NO: 2, said method comprising:*

*(a) obtaining a biological sample from the alimentary canal or body fluids of a subject,*

*(b) contacting said sample with a binding molecule which immunoreacts with a targeting partner having an amino acid sequence set forth in SEQ ID NO: 1 or SEQ ID NO: 2,*

*(c) observing the formation of said molecular complex wherein the extent of complex formation is diagnostic of said alimentary canal or epithelium-related dysfunction.*

*15. The molecular complex of claim 14, wherein said biological sample is selected from alimentary canal tissue or body fluids selected from the group consisting of epithelium tissue of alimentary canal, peripheral blood, serum, urine and stool.*

*16. The molecular complex of claim 15, wherein said binding molecule is a portion of Fab, Fab', $F(ab')_2$ or a fragments thereof.*

*17. The molecular complex of claim 6, wherein said binding molecule is prepared by a method comprising:*

*(a) obtaining cells from an animal immunized with a tropomyosin isoform (TI) protein, or a fragments thereof having an amino acid sequence set forth in SEQ ID NO: 1 and/or SEQ ID NO: 2,*

*(b) fusing said cells with cells from a self-perpetuating cell line to form fused hybrid cell colonies,*

*(c) identifying the hybrid cells colonies that produce binding molecules that immunoreact with targeting partners having the amino acid sequence set forth in SEQ ID NO:1, and*

*(d) culturing said hybrid cells colonies identified in step (c).*

* * * * *